(12) United States Patent
Sinbar et al.

(10) Patent No.: US 9,008,408 B2
(45) Date of Patent: Apr. 14, 2015

(54) METHOD AND SYSTEM FOR DETERMINING THE QUALITY OF PHARMACEUTICAL PRODUCTS

(75) Inventors: Eran Sinbar, M.P. Misgav (IL); Yoav Weinstein, Atlit (IL)

(73) Assignee: D.I.R. Technologies (Detection IR) Ltd., Haifa (IL)

( * ) Notice: Subject to any disclaimer, the term of this patent is extended or adjusted under 35 U.S.C. 154(b) by 397 days.

(21) Appl. No.: 13/147,867

(22) PCT Filed: Feb. 4, 2010

(86) PCT No.: PCT/IL2010/000102
§ 371 (c)(1),
(2), (4) Date: Aug. 4, 2011

(87) PCT Pub. No.: WO2010/089744
PCT Pub. Date: Aug. 12, 2010

(65) Prior Publication Data
US 2011/0293166 A1 Dec. 1, 2011

Related U.S. Application Data

(60) Provisional application No. 61/202,204, filed on Feb. 5, 2009, provisional application No. 61/263,549, filed on Nov. 23, 2009.

(51) Int. Cl.
| | | |
|---|---|---|
| G06T 7/00 | (2006.01) |
| G01N 21/35 | (2014.01) |
| G01N 25/00 | (2006.01) |
| G01N 33/15 | (2006.01) |
| G01N 21/3554 | (2014.01) |
| G01N 21/95 | (2006.01) |
| G01N 25/72 | (2006.01) |

(52) U.S. Cl.
CPC ............ *G01N 33/15* (2013.01); *G01N 21/3554* (2013.01); *G01N 21/9508* (2013.01); *G01N 25/72* (2013.01)

(58) Field of Classification Search
None
See application file for complete search history.

(56) References Cited

U.S. PATENT DOCUMENTS

| | | | |
|---|---|---|---|
| 4,026,656 A | | 5/1977 | Kusz et al. |
| 4,795,906 A | | 1/1989 | Adams et al. |
| 4,965,451 A | | 10/1990 | Solter |
| 5,113,073 A | | 5/1992 | Szepan |
| 5,357,112 A | * | 10/1994 | Steele et al. .................. 250/340 |
| 5,417,494 A | * | 5/1995 | Kempa et al. ...................... 374/5 |

(Continued)

FOREIGN PATENT DOCUMENTS

| | | |
|---|---|---|
| CA | 1 145-711 | 5/1983 |
| CA | 2 267 586 | 10/1999 |

(Continued)

OTHER PUBLICATIONS

ThermaCAM SC Series Infrared Cameras for Research and Development: Features/Specifications. FLIR Systems, 2001, 47 pages.*

(Continued)

*Primary Examiner* — Jon Chang
(74) *Attorney, Agent, or Firm* — Frommer Lawrence & Haug LLP; William S. Frommer

(57) ABSTRACT

Thermographic imaging is used to monitor quality parameters of pharmaceutical products in a manufacturing process.

12 Claims, 18 Drawing Sheets

(56) References Cited

U.S. PATENT DOCUMENTS

| | | | |
|---|---|---|---|
| 5,458,418 A * | 10/1995 | Jones et al. | 374/45 |
| 5,646,405 A * | 7/1997 | Nevel et al. | 250/341.6 |
| 5,818,951 A * | 10/1998 | Schivley | 382/100 |
| 5,834,661 A * | 11/1998 | Nonaka et al. | 73/866 |
| 5,978,691 A | 11/1999 | Mills | |
| 6,013,915 A * | 1/2000 | Watkins | 250/341.1 |
| 6,224,699 B1 | 5/2001 | Bett et al. | |
| 6,297,508 B1 * | 10/2001 | Barmore et al. | 250/459.1 |
| 6,316,772 B1 | 11/2001 | Egelberg | |
| 6,395,538 B1 | 5/2002 | Naughton et al. | |
| 6,541,271 B1 | 4/2003 | McFarland et al. | |
| 6,614,531 B2 | 9/2003 | Sato et al. | |
| 6,771,369 B2 | 8/2004 | Rzasa et al. | |
| 6,853,447 B2 | 2/2005 | Goetz | |
| 7,006,214 B2 | 2/2006 | Rzasa et al. | |
| 7,028,723 B1 | 4/2006 | Alouani et al. | |
| 7,046,359 B2 | 5/2006 | Voigt et al. | |
| 7,126,685 B1 | 10/2006 | Paige et al. | |
| 7,218,395 B2 | 5/2007 | Kaye et al. | |
| 7,227,148 B2 | 6/2007 | Sato et al. | |
| 7,317,526 B2 | 1/2008 | Voigt et al. | |
| 7,364,696 B1 | 4/2008 | Sarvazyan | |
| 7,434,986 B2 | 10/2008 | Ignatowicz | |
| 7,462,809 B2 | 12/2008 | DiMarzio et al. | |
| 7,730,797 B1 * | 6/2010 | Deolalikar et al. | 73/865.8 |
| 2002/0128797 A1 * | 9/2002 | Sun | 702/172 |
| 2002/0166970 A1 * | 11/2002 | Komulainen et al. | 250/340 |
| 2002/0172410 A1 * | 11/2002 | Shepard | 382/141 |
| 2004/0021861 A1 | 2/2004 | Lewis et al. | |
| 2004/0135086 A1 | 7/2004 | Lewis et al. | |
| 2005/0108044 A1 | 5/2005 | Koster | |
| 2005/0169511 A1 | 8/2005 | Jones | |
| 2005/0243305 A1 | 11/2005 | Vig et al. | |
| 2005/0276907 A1 | 12/2005 | Harris et al. | |
| 2005/0286606 A1 | 12/2005 | Ignatowicz | |
| 2006/0278831 A1 * | 12/2006 | Matsumoto et al. | 250/341.1 |
| 2006/0289766 A1 | 12/2006 | DeMarzio et al. | |
| 2007/0118324 A1 | 5/2007 | Gulati | |
| 2008/0022632 A1 | 1/2008 | Gysi et al. | |
| 2008/0149725 A1 * | 6/2008 | Rosenbaum | 235/462.41 |
| 2008/0197284 A1 | 8/2008 | Ebenstein et al. | |
| 2008/0274028 A1 * | 11/2008 | Lin et al. | 423/263 |
| 2012/0013734 A1 | 1/2012 | Ranieri et al. | |
| 2012/0279968 A1 | 11/2012 | Levy Sarraf et al. | |

FOREIGN PATENT DOCUMENTS

| | | |
|---|---|---|
| CN | 1292871 A | 4/2001 |
| CN | 2661526 | 12/2004 |
| DE | 196 29 101 | 1/1998 |
| DE | 199 08 410 | 5/2000 |
| EP | 0 355 699 | 8/1989 |
| EP | 2180744 | 3/2002 |
| EP | 1 623 930 | 6/2005 |
| EP | 1 560 009 | 8/2005 |
| EP | 1 719 970 | 8/2006 |
| EP | 1 882 579 | 1/2008 |
| EP | 1 188 385 | 2/2012 |
| EP | 2 520 909 | 4/2012 |
| EP | 2 453 225 | 5/2012 |
| FR | 2323143 | 4/1977 |
| JP | 01-242947 | 9/1989 |
| JP | 8-184571 | 7/1996 |
| JP | 09-297114 | 11/1997 |
| JP | 10-278910 | 10/1998 |
| JP | 2002-211058 | 7/2002 |
| JP | 2003-247963 | 9/2003 |
| JP | 2003-307505 | 10/2003 |
| JP | 2005-526998 | 8/2005 |
| JP | 2006-119134 | 5/2006 |
| JP | 2006-177869 | 7/2006 |
| JP | 2006258551 | 9/2006 |
| JP | 2007502978 | 2/2007 |
| JP | 2007-108110 | 4/2007 |
| JP | 10-318955 | 12/2010 |
| KR | 10-2004-0103198 | 12/2004 |
| RU | 2 015 507 | 4/1991 |
| RU | 2068557 | 10/1996 |
| RU | 2125259 | 10/1997 |
| RU | 48453 | 12/2004 |
| RU | 2248736 | 3/2005 |
| RU | 2 301 415 | 8/2005 |
| SU | 534120 | 12/1974 |
| SU | 1193555 | 5/1984 |
| SU | 1635099 | 4/1989 |
| WO | WO 96/18978 | 6/1996 |
| WO | WO 98/02729 | 1/1998 |
| WO | WO 00/67204 | 11/2000 |
| WO | WO 03/062809 | 7/2003 |
| WO | WO 03/100714 A1 | 12/2003 |
| WO | WO 2005/019863 | 3/2005 |
| WO | WO 2005/040739 | 5/2005 |
| WO | WO 2006/090353 | 8/2006 |
| WO | WO 2007/147158 | 12/2007 |
| WO | WO 2008/021520 | 2/2008 |
| WO | WO 2008/140473 | 11/2008 |
| WO | WO 2009/019698 | 2/2009 |
| WO | WO 2010/120555 | 10/2010 |
| WO | WO 2013/057731 | 4/2013 |

OTHER PUBLICATIONS

Lyon et al. "Near-Infrared Spectral Imaging for Quality Assurance of Pharma-ceutical Products: Analysis of Tablets to Assess Powder Blend Homogeneity." AAPS PharmSciTech, 3(3) article 17, 2002, pp. 1-15.*

Bechard, Simon R. and Down, G.R.B.; "Infared Imaging of Pharmaceutical Materials Undergoing Compaction"; *Pharmaceutical Research*. 1992; v. 9; No. 4; 521-528.

Waite, G., "Non-Destructive Testing with Thermographic Techniques". Technisches Messen TM, vol. 66 No. 9 (1999), p. 312-321.

Gergenova Z.V., et al., Infrared Thermographic Nondestructive Testing System. XI Modern Technique and Technologies 2005,pp. 182-183, (XP031244843).

Wolff et al., NIR-Based Chemical Imaging as an Anticounterfeiting Tool. PharmaManufacturing.com, 2012.

T. Puchert et al. "Near-infrared chemical imaging (NIR-CI) for counterfeit drug identification—A four-stage concept with a novel approach of data processing (Linear Image Signature)". Journal of Pharmaceutical and Biomedical Analysis, vol. 51, Issue 1, Jan. 5, 2010.

*Dynamic infrared thermal mapping*; Radiotekhnika, 1991, #8; p. 54, para. 3.

International Search Report issued in corresponding International Application No. PCT/IL2014/050496, mailed Oct. 23, 2014.

International Search Report issued in corresponding International Application No. PCT/IL2014/050396, mailed Jul. 3, 2014.

"Super Seal™ Max extends shelf life and seals Jus-Made's diverse product mix"; NEWS Cap Sealing Technology, Oct. 5, 2007, XPO55125438, http://www.enerconind.com/mediaLib/csm.

Clausing, et al.; "Get the Full Picture of Thermal Imaging—An Infrared Camera Can Shed Light on a Variety of Plant Issues"; Chem pross, v.69, No. 4, Apr. 2006, pp. 32-35.

* cited by examiner 2 mm   1mm

Dry

Wet

High moisture content

Low moisture content

High moisture content

Dry

Non-compact

Compact

20°C

25°C

Genuine    counterfeit

10mg

20mg

METHOD AND SYSTEM FOR DETERMINING THE QUALITY OF PHARMACEUTICAL PRODUCTS

FIELD OF THE INVENTION

This invention relates to manufacturing processes and in particular to authenticity and quality assurance (QA) of manufacturing processes and their products.

BACKGROUND OF THE INVENTION

Process Analytical Technologies (PAT) has been defined by the United States Food and Drug Administration (FDA) as a mechanism to design, analyze, and control pharmaceutical manufacturing processes through the measurement of critical process parameters which affect critical quality attributes. The concept aims at understanding the processes by defining their critical process parameters, and accordingly monitoring them in a timely manner thus resulting in a more efficient quality assurance test with reduced over-processing and enhanced consistency.

Various spectroscopic methods currently used in PAT provide a fingerprint by which a molecule can be identified. Near Infra Red spectroscopy (NIRS) which is based on molecular overtone and combination vibrations utilizes the near infrared region of the electromagnetic spectrum to characterize various molecules. Raman spectroscopy relies on inelastic scattering of photons by molecules to study vibrational, rotational and other low-frequency modes in a system.

Several publications discuss the utilization of IR spectroscopy during manufacturing processes.

U.S. Pat. No. 6,395,538 to Naughton R. A. et al. discloses a method and a system for providing real-time, in situ biomanufacturing process monitoring and control in response to IR spectroscopy.

U.S. Pat. No. 6,853,447 to Goetz A. discloses a method for verifying the contents of a package of materials such as pharmaceutical or food, the method utilizes an array of IR imaging spectrometers.

U.S. Pat. No. 7,126,685 to Paige M. E. et al. discloses a spectroscopy method for characterizing a sample in container such as a pharmaceutical bottle.

DE 19908410 describes a process for testing if an article is authentic characterized in that a tested article is heated up to a predetermined temperature and using a heat radiation sensitive device, the heat emitted from the article is detected and used for determining the authenticity of the article.

DE 19629101 describes a unit for identification, inspection and control of packaging and their content by means of temperature sensitive sensors and IR cameras, used also for spotting and removal of faulty containers.

The FDA's PAT initiative encourages the development of new analytical technologies for constant monitoring of pharmaceutical manufacturing processes.

SUMMARY OF THE INVENTION

The present invention is based on a novel concept of utilizing thermographic imaging for monitoring manufacturing process so as to assure quality of materials obtained in these processes.

Thus, in one aspect, the present invention provides a method for determining quality of material obtained in a manufacturing process comprising:

(a) generating an infrared (IR) image of said material by an IR detector operable to sense, in its field of view, radiation of said material in a mid to very long IR wavelength;

(b) processing the IR image to generate an output indicative of the quality of said material; and (c) displaying said output or utilizing said output to alter the manufacturing process or a combination of same.

In another aspect, the present invention provides a system for determining quality of material obtained in a manufacturing process comprising:

(a) an IR image generating device comprising an IR detector operable to sense, in its field of view, radiation of said material in a mid to very long IR wavelength and to generate therefrom a respective IR image of said material;

(b) a processing utility for processing said IR image to generate an output indicative of the quality of said material;

(c) a control unit configured to displaying said output or to utilize said output to alter the manufacturing process or a combination thereof.

Also within the scope of the present invention there is provided a method for determining authenticity of a package or quality of a package comprising;

(a) generating one or more images of said package by a near IR (NIR), ultraviolet (UV) or ultrasound (US) detector, operable to detect, in its field of view, said package;

(b) comparing said one or more images of said package with a reference package; and (c) displaying said comparison or a quantitative value indicative of said comparison, thereby enabling determination the authenticity of said package.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 11B is displayed in FIG. 11D.

DETAILED DESCRIPTION OF EMBODIMENTS

Figure 1A:
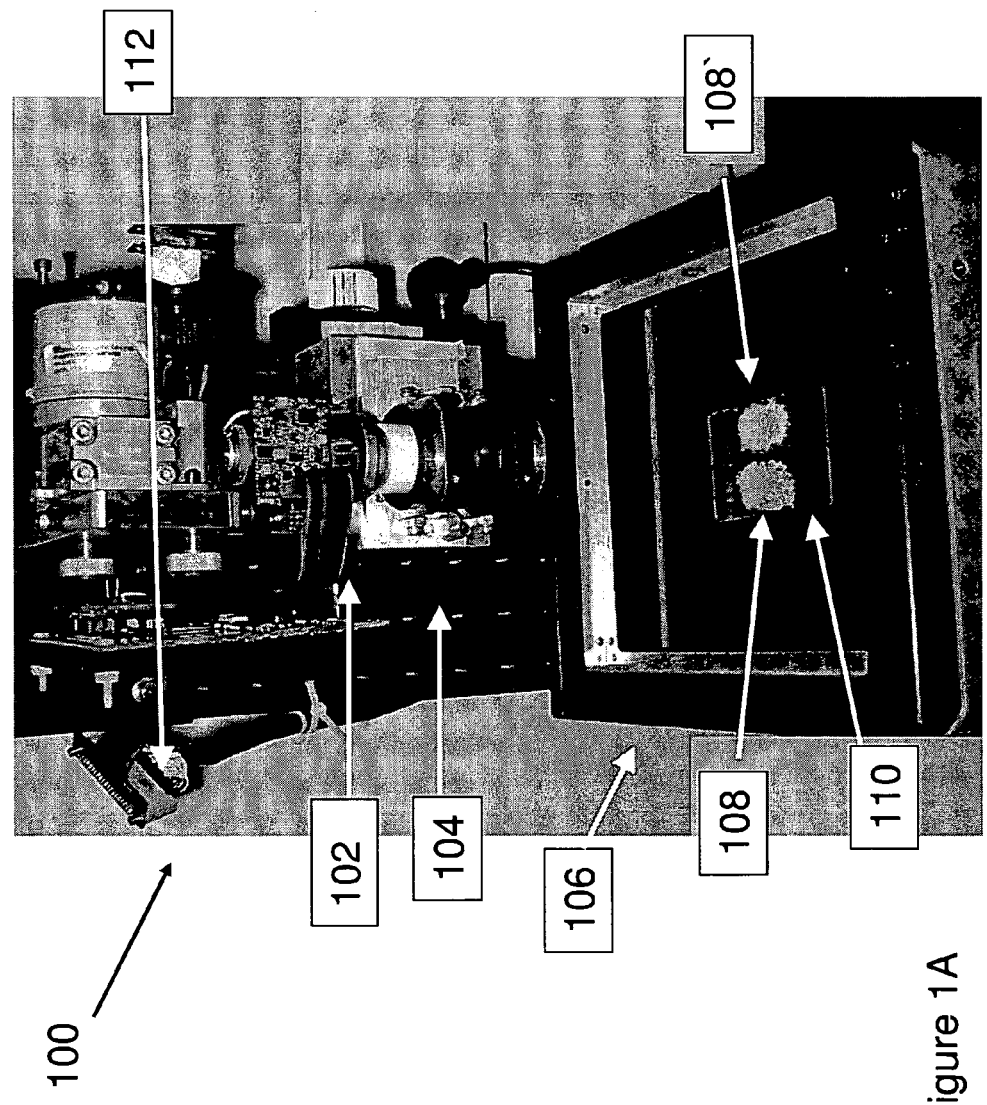
FIGS. 1A-1B show two prototype systems used in the non-limiting examples of the invention, the first prototype making use of a cooled, InSb detector (FIG. 1A) and the second prototype making use of an un-cooled VOx detector (FIG. 1B).

Thermographic imaging (also known by the term "thermal imaging") is a type of infrared imaging in which radiation emitted from a material is detected based on the temperature and emissivity at different locations across the material (according to the black body radiation law) and images are produced according to said detected temperatures and emissivity. Specifically, the amount of radiation emitted by a material increases with temperature; therefore thermography allows one to see variations in temperature and emissivity. When viewed by thermographic camera, warm material stand out well against cooler backgrounds.

Thus, in accordance with one aspect, the present invention provides a method for determining quality of material obtained in a manufacturing process comprising:

(a) generating an infrared (IR) image of said material by an IR detector operable to sense, in its field of view, radiation of said material in a mid to very long IR wavelength;

(b) processing the IR image to generate an output indicative of the quality of said material; and (c) displaying said output or utilizing said output to alter the manufacturing process or a combination of same.

In accordance with another aspect, the present invention provides a system for determining quality of material obtained in a manufacturing process comprising:

(a) an IR image generating device comprising an IR detector operable to sense, in its field of view, radiation of said material in a mid to very long IR wavelength and to generate therefrom a respective IR image of said material;

(b) a processing utility for processing said IR image to generate an output indicative of the quality of said material;

(c) a control unit configured to displaying said output or to utilize said output to alter the manufacturing process or a combination thereof.

In some embodiments, the radiation of the material may be in a range of wavelengths selected from mid IR to very long IR. In other embodiments, the radiation of the material may be in a specific wavelength selected from mid IR, long IR and very long IR wavelength. To this end, the system may include one or more IR filters as further discussed below.

The method and system of the invention may be applicable with respect to the manufacturing of any material, for which quality assurance is desired. The term "material" as used herein includes a single substance as well as a combination of substances, constituting a starting (raw) material (e.g. to identify and confirm incoming raw material), an intermediate material, as well as the final product in processes taken place in the manufacturing of said final product. At times the term "product" is used interchangeably with the term "material" or "package" (in the latter, when referring, for instance, to the final product in a manufacturing process).

As appreciated by those versed in industry, there could be a non-limiting list of final products for which the method of the invention is applicable. Some such final products may include, a pharmaceutical product, such as a drug; a cosmetic product; a piece of jewelry (to determine the quality of the jewelry, e.g. the purity of the material from which it is made); an agrochemical product, a beverage e.g., soft drink, milk, water, wine, a food, e.g. fish, meat, bread, or food supplement product, e.g. sugar, flower; fuel (components or purity thereof), paint product; or any other product, the quality of which needs to be determined. It is noted that the method and system of the invention may be applicable for determining the presence of foreign objects in such products to ensure the quality of the product.

As used herein, the term "foreign object" denotes any object or particulate matter that is not intended to be included in the material product. The foreign object may be an object derived from the source of the product, e.g. residual bones in a fillet product, or may be unintentionally introduced into the material during is preparation, Non-limiting examples of such objects may include plastic, glass, sand, residual bones or bone particles.

The invention may also be applicable for verifying quality of product following storage, and/or determining whether the storage condition of a product were appropriate based on the quality of the product following said storage. The parameters of the storage that may be determined based on the method of system of the invention may include, without being limited thereto, humidity and/or temperature during storage.

The invention may also be applicable for determining quality of a product in case it is a fake product, e.g. in counterfeit actions. For instance, the final product may be a package to be analyzed in accordance with the invention vis-à-vis a package of an authentic product, as will be further discussed below.

Further, in the context of the present invention the final product may also refer to validating a drug to be given to a patient in drug stores, hospitals etc. (i.e. verifying that indeed this was the intended drug/dosage to be given to the patient). This is of particular relevance in places where the drugs to be distributed are not packed in individually sealed packages with a label but rather are provided to the distributor in large containers. As it happens, at times, in drug stores, different drugs from different containers may be unintentional mixed and the method and system of the invention may be used to verify that notwithstanding this unintentional mixing, the costumer received the correct medication.

Furthermore, the method and system of the invention may be used to ensure correlation between the label on a product, i.e. on a package, and the product contained therein as well as to ensure proper packaging and/or for detecting defects, such as holes or ruptures in the package of the product, such defects undetectable by the eye.

In one preferred embodiment, the product is a therapeutic drug and the method and system of the invention are applicable for determining quality assurance of the manufacturing processes of the therapeutic drug.

The IR image generated is a thermographic (thermal) image which may be generated by passive thermography or by active thermography.

The term "passive thermography" is understood to denote the generation of an image of radiation emitted from the material at a steady state temperature (i.e. without a priori heating or cooling the material). The term "active thermography" is understood to denote the generation of one or more IR images of a material after the material is exposed to heating or cooling (e.g. thermal pulse, continuous thermal radiation or through periodic (sinusoidal) modulation) so as to change the temperature of the material from a steady state equilibrium condition to a non stable condition.

In one embodiment, the method and system of the invention utilize active thermography, namely, the method and system involve the application of a least one thermal pulse onto the material. The thermal pulse may be applied by radiation, or in the form of temperature conduction, temperature convection, friction etc., or any other applicable manner of inducing temperature change on a target material. The thermal pulse results in the change of the material's temperature, either by applying heat onto the material or cooling the material or by a combination of same, e.g. heating and then cooling or cooling and then heating (e.g. delta function).

The thermal pulse may be applied onto the material as a single thermal pulse, e.g. a heating pulse or a cooling pulse, a sequence of two or more thermal pulses, as well as periodic modulation. The pulse may take from less than a second to even up to several minutes (typically less than 3 minute).

Thermal pulse may be applied onto the material by various thermal pulse generators known in the art. Without being limited thereto, such devices may include laser beam, IR lamp, microwave, ultrasonic waves, cooling chamber, heating oven, thermal electronic cooler (TEC) (for cooling as well as heating), Black Body radiating source (for cooling as well as heating), gas expansion (for cooling as well as heating), refrigerator and thermal stabilizing chamber.

It is noted that in accordance with the invention, the material can be heated, cooled or a combination of same. It is nonetheless essential that the heating or cooling is not above or below (respectively) a predetermined temperature threshold at which the material may be damaged, e.g. decomposition by excessive heating or condensation or freezing by excessive cooling. Such temperature threshold would typically be provided by the manufacturer of the authentic material. Further, it is noted that in one preferred embodiment, the material is cooled, e.g., to about 15° C., said cooling is optionally followed by heating the material to room temperature (~22° C.-~25° C.) or to a temperature above room temperature, e.g. and without being limited thereto, to between about 30° C. to about 35° C.

Active thermography may be used in several configurations. For instance:

Reflection: the surface of the material may be heated and/or cooled and simultaneously IR reflected from the surface of the material is detected; heating and/or cooling the surface of the material, removing the heat or cooling source and then detecting the IR radiation emitted from the surface of the material;

Bulk heating/cooling: heating and/or cooling the entire material (e.g. in a heating or cooling chamber), and detecting simultaneously or subsequent to heating and/or cooling, IR radiation of the heat transmitted from the bulk of the material (bulk emission).

Transmission: the back surface of the material may be heated and/or cooled and the transmitted heat/cool pulse is measured from the front surface of the material.

In one embodiment, the thermal pulse applied onto the material is a thermal pulse in the form of, without being limited thereto, a delta function thermal pulse, step function thermal pulse, rectangular function thermal pulse, saw tooth function thermal pulse, periodic function thermal pulse or combination of same.

The method and system of the invention permit the generation of an IR image by the use of an image generating device comprising an IR detector operable to sense, in its field of view, radiation of the material in a mid wave IR (MWIR) to very long wave IR (VLWIR). In the context of the present invention, radiation includes from 3 µm to about 20 µm, namely, including the MWIR being between 3 to 5 µm; LWIR being between 8 to 12, or 7 to 14 µm; and VLWIR being, for the purpose of the present invention, between 12 to about 20 µm. In the present invention the inherent tendency of water molecules to absorb radiation emitted from bodies in the range of 5 to 8 µm may be used to detect the presence of water molecules in the tested samples (e.g. to identify areas of humidity in a sample). Such detection is possible in the instant invention (as opposed to far distance detection of objects) due to the relatively short distance (typically from centimeters to several meters) between the tested sample and the detector, in such distance the atmospheric absorption of water molecules is negligible and hence does not interfere with the detection.

The IR images may be generated by a variety of devices known in the art. Typically, albeit not exclusively, an IR image is generated by the use of a focal plane array (FPA) which is an image sensing device comprising an array of light sensing pixels at the focal plane of a lens. To this end, the IR detector is operable in combination with an optical arrangement. The optical arrangement may comprise, lenses for focusing the radiation of said material on the IR detector or any other optical device capable of focusing the IR radiation by refraction, reflection, pinhole, diffraction, etc; filters, for limiting sensed radiation to a defined spectrum range; polarizers, for converting any unpolarized or mixed polarization beam into a beam with a single polarization state (e.g. tunable polarizers); diffusers for scattering light etc. Generally, while the use of a FPA is preferable in the instant invention, at times, the use of single pixel detector may be of choice. To this end, the single pixel detector can be used in combination with an arrangement of mirrors placed such that an image of the sample is obtained.

The optical arrangement, as known to those versed in the art, may be adjusted to capture IR reflection as well as IR transmission. The IR radiation is emitted from the surface of the product and may reflect the temperature of the surface as well as that of the bulk material.

The IR detector in combination with the optical arrangement may be utilized to generate a gray scale or colored IR image. In addition, while typically the image is a two dimensional (2D) image, the method may equally be used for generating a three dimensional (3D) [x,y,time(frame)] image. The 3D image may take into consideration for example the time, wavelength, polarization as an additional parameter for creating the image. The method may further be used for generating a four dimensional (4D) image for example by applying chemical imaging as a function of time [x,y,signal ($\lambda$)/time(frame)]. Thus, the image may be generated by the combination of the coordinates [x,y] with one or more of the time, wavelength and polarization.

In one embodiment, the system and method of the invention may include a tunable band pass filter for applying thermography based-chemical imaging in the MWIR to VLWIR. Thermography-based chemical imaging refers to the generation of an image from a series of images at different wavelengths. Accordingly, each pixel in the image denotes (in the spectral dimension, namely, the 3D) the spectral behavior of a point on the imaged entity e.g. as a result to an applied thermal (chemical imaging can be obtained with active as well as passive thermography). The chemical image is obtained by measuring the thermographic signal (passive or active) with a tunable filter and then building out of it a 3D image. In addition, a fourth dimension may be taken into consideration, namely, the time, so as to obtain a 4D image based on [x,y,signal($\lambda$),time(frame)].

The IR detector including the optical arrangement is typically referred to as an IR (thermographic) camera. The most common types of IR cameras that utilize FPA are, without being limited thereto, an Indium antimonide (InSb) camera, Indium gallium arsenide (InGaAs) camera, mercury cadmium telluride (MCT) (HgCdTe) camera, or quantum well infrared photodetector (QWIP) camera, uncooled Vanadium Oxide (VOx) camera, and un-cooled amorphous silicon (aSi) camera.

The IR image obtained using the thermographic camera is then processed into an output indicative of the quality and/or authenticity of the imaged material. The output may be in the form of an image to be displaced on a suitable display unit, e.g. for visual inspection and decision making by a user, or the output comprises one or more parameters of the material indicative of the quality of the material, i.e. one or more parameters characterizing the imaged material is processed by a dedicated IR image processing utility. The parameter, referred to herein by the term "material's parameter" is used to denote any characterizing feature of the material (obtained in the manufacturing process) that provides information regarding the quality of the material. The parameter may include, without being limited thereto, one or more selected from the group consisting of moisture content, moisture dispersion, material's density, material's particle size as well as size distribution, polymorphic structure, crystal structure, temperature as well as temperature distribution, homogeneity (in terms of size, temperature, blending homogeneity etc.), morphology, texture, porosity, proper coating of products (e.g. in the production of coated tables or capsules—to ensure that the coating is uniform), missing material, e.g. when a tablet is missing in a closed blister or liquid is missing or less than required in a container; material integrity, e.g. when a product is fractured, broken or incomplete; authenticity of the material and any other characterizing feature of the material that may be deduced from the IR image.

The parameter(s) may be in the form of a comparable value, i.e. a value that may be compared to a predetermined threshold parameter. The term "predetermined threshold parameter" is used herein to denote an essentially distinct value (namely a distinct integer±standard deviation) or a range of values, predetermined based on reference materials with qualities that are approved by required standards for the same material.

Image processing may make use of image contrast analysis, edge detection, image arithmetic, cross correlation between images, convolution between images or between an image to a predefined kernel, spatial frequency transformation and/or spatial filtering methods, temporal frequency transformation and temporal filtering methods, Fourier transforms, discrete Fourier transforms, discrete cosine transforms, morphological image processing, finding peaks and valleys (low and high intensity areas), image contours recognition, boundary tracing, line detection, texture analysis, histogram equalization, image deblurring, cluster analysis etc., all as known to those versed in the art of image processing.

In one embodiment, the image processing is performed using MATLAB (The Mathworks, Inc) software. As appreciated, any image or signal processing algorithm known in the art may be equally applied in the context of the present invention. The analysis may be in the spatial domain or time domain or both.

In one embodiment, the outputs are in the form of a coordinate (x,y) or plurality of coordinates [($x_i$, $y_i$), ($x_z$, $y_z$) . . . ], e.g. for indicating where anomalies exist in the image of the material under examination as compared to a predetermined threshold.

The predetermined threshold parameter can be also an image in a database which is compared to the image of the measured object, and if the correlation between the two images is above a predefined threshold it is considered authentic, if not it is considered as low quality/miss-match or counterfeit.

The material's parameter, as deduced from the captured IR image, is then correlated (compared) to the threshold parameter, predetermined for the specific manufacturing process, the correlation resulting in an output corresponding. For example, when the material's parameter is statistically significantly different from the threshold parameter (according to conventional statistical tests, such as the t-test, with value equal or lower than 0.5, at times 0.1, or even 0.05), the output corresponds to a defected material; when the material's parameter is within the threshold parameter, the output corresponds to a material with a desired quality.

It is noted that the thermographic image obtained in accordance with the present invention may also be processed by combining it with an image obtained in wavelengths selected from one or more of near IR (NIR, using e.g. a silicon, InSb or InGaAs detectors), visible (VIS, using e.g. CCD camera), ultra violate (UV, using UV detectors), Terahertz (using Terahertz detectors), and ultrasound (US) using conventional ultrasound detectors to form what is known in the art as Image fusion. The resulting combined image may be a fusion of such images. Fusion of images may be fusion of the whole image or of selected parts of the image. Image fusion techniques are known in the art and include any device that can superposition two or more images one on top of the other.

In accordance with the invention, the output may be displayed and/or cause alteration of the process. For example, when the output corresponds to a defected material, i.e. a material with low quality that cannot be further processes towards the final product, or cannot be considered as a final product with a satisfactory quality the process may be altered by ceasing the process, repeating the process, directing the material to a different manufacturing process, altering process conditions, etc. In addition, a suitable notification regarding the low quality of the material may be generated and this notification may be displayed on a visual display unit (e.g. monitor) and/or by generating an audio alert (using an audio device).

In one embodiment, the system of the invention comprises a memory for one or more of storing a database of predetermined threshold parameters of manufacturing processes, for recording history of manufacturing processes and their corresponding outputs; processes alterations; etc.

In operation, the material's parameter may be compared to a predetermined threshold parameter from the database or to a predetermined threshold parameter defined by the user (the operator of the system) prior to initiating the manufacturing processes, e.g. by the use of a user interface allowing input of desired conditions and/or threshold parameters for the specific manufacturing process. The material's parameter is then correlated with a threshold parameter from said database or as introduced into the system.

The result of correlation provide an On Line output. In other words, when the output is indicative that the material is defective, the system is configured to immediately alert the user and at times, automatically alter the manufacturing process. Similarly, when the output is indicative that the material is of a desired quality, a corresponding notification may be generated and the material may then be automatically forwarded to a next stage of processing or finalization.

It has further been envisaged by the inventors that quality and thereby authenticity of a packed product may be even determined via analysis of an image of the package captured in even only one of the following wavelengths: NIR (using e.g. a silicon, InSb, InGaAs detectors or VOx uncooled detectors, MWIR (using e.g. a InSb detector); VIS (using e.g. CCD camera), UV (using UV detectors; Terahertz (using Terahertz detectors), and US (using conventional ultrasound detectors). In order to obtain an image in one or more of these wavelengths, the product is preferably exposed to light (mostly when the image is generated using a detector in the NIR and/or VIS spectra) and then the image is captured from the reflected light. In some embodiments light illumination is halogen light illumination e.g., 35 Watt; in other embodiments light illumination is light emitted from an electric bulb lamp; in yet other embodiments the light is a UV light.

Thus, in a further aspect according to the invention there is provided a method for determining authenticity of a package or quality of a package the method comprises:
  (a) generating one or more images of the package by a visible (VIS) detector, near IR (NIR) detector, ultraviolet (UV) detector, ultrasound (US) detector, MWIR detector or Terahertz detector operable to detect, in its field of view, the said package, wherein when said one or more images is generated by a VIS detector or by the NIR detector, said package is illuminated during image generation and wherein when said one or more images is generate by a VIS detector said illumination is by UV light;
  (b) comparing said one or more images of the package with a reference package (e.g., an image of an authentic package); and
  (c) displaying the comparison or a quantitative value indicative of the comparison, thereby enabling determination the authenticity of the package.

For performing the above method for determining authenticity of a package or quality of a package the same system described above may be used, with the exception that the detector is one of NIR, VIS, UV, Terahertz, and US detector.

In some preferred embodiments the method for determining authenticity of a package or quality of a package comprises illuminating the package during capturing of said one or more images.

In some further embodiments illumination is performed using a light source selected from the group consisting of halogen light, UV light, and electric bulb, without being limited thereto.

As described above, the system of the invention comprises several components including the IR image generator (including the IR detector), the optical arrangement, the processing utility, the memory, the user interface, etc. As appreciated by those versed in the art, these components may communicate using wired or wireless communication module.

Reference is now made to FIG. 1A exemplifying a thermographic imaging system according to one embodiment of the invention. According to the figure, a system (100) includes, inter alia, a cooled detector, specifically an Indium-Antimonide (InSb) IR detector (102) manufactured by SCD (Semi Conductor Devices), an optical arrangement (104) manufactured by OPHIR optics and a Black Body radiating source (106) manufactured by CI instruments. The tested materials (108 and 108') are placed on a flat glass plate (110) on top of the Black Body radiating source (106). The system also includes a processing utility (112) for processing the IR image to generate an output indicative of the quality of said material. The processing utility is used to convert the analog signal obtained from the detector (102) into a digital signal and to convert a series of digital signals into an image format. The system also includes a control unit (not illustrated in the figure) for operating the aforementioned components and for displaying said output or to utilize said output to alter the manufacturing process or a combination thereof.

Figure 1B:
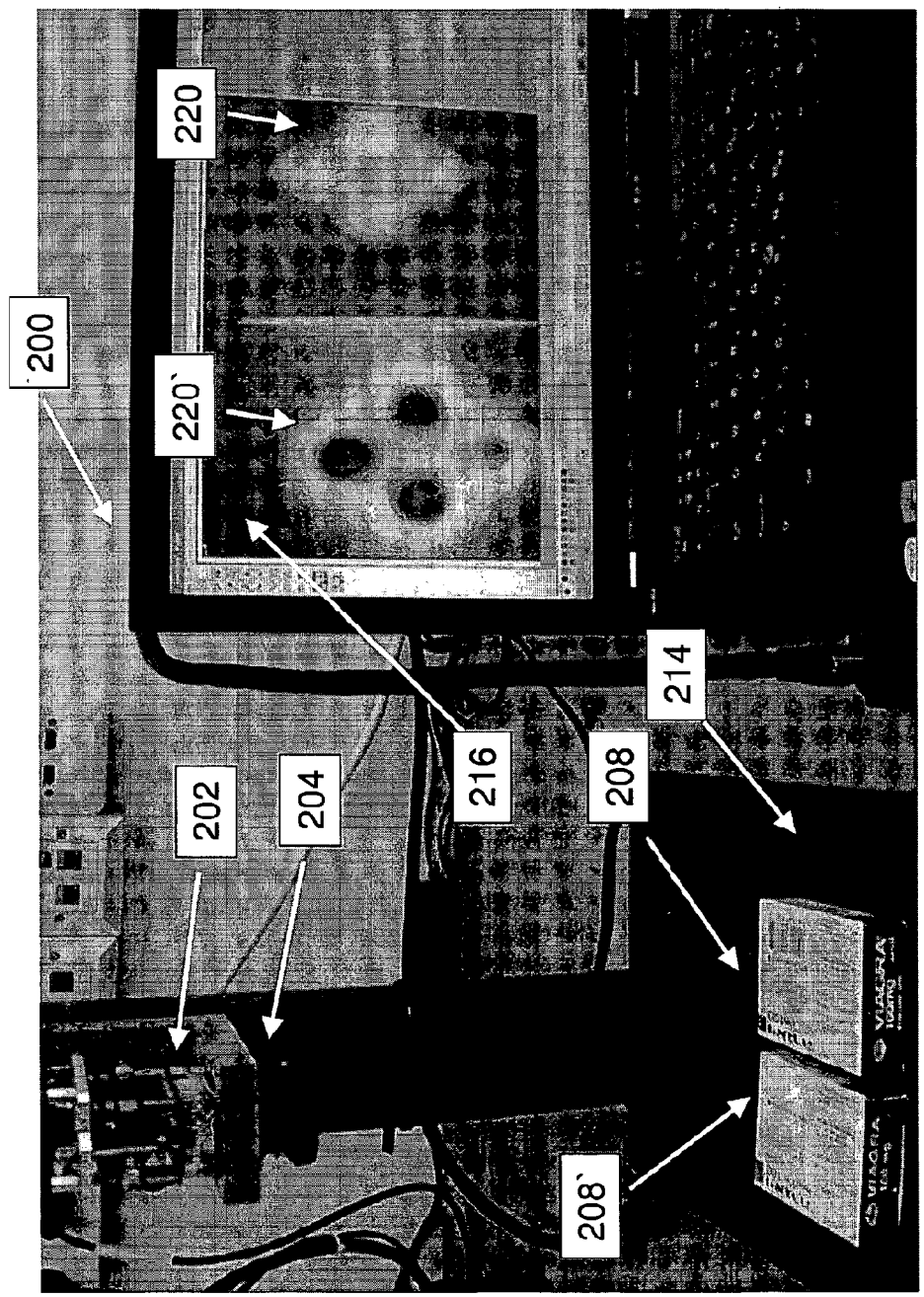

In the particular embodiment illustrated in FIG. 1A, the detector (102) comprises a cooled detector, typically, albeit, not limited to, detection of radiation in the MWIR region. Similarly, the system may include an uncooled detector, typically, albeit, not limited to, detection of radiation in the LWIR as well as the VLWIR range. In this connection, FIG. 1B illustrates a system 200 making use of an un-cooled detector. For simplicity, like reference numerals to those used in FIG. 1A, shifted by (100) are used to identify components having a similar function in FIG. 1B. For example, cooled detector (102) in FIG. 1A is replaced with an un cooled VOx detector (202) in FIG. 1B. FIG. 1B shows a sample holder (214) onto which an authentic drug package (208) an a fake package (208') are placed; an un-cooled VOx detector (202) and an optical arrangement (204). Also illustrated is a control and display unit (216). In this particular example the tested samples are not placed on a black body but rather were cooled prior to image capturing. The difference in the product within the packages is exhibited on a monitor where an image of the authentic drug package (208) is illustrated as image (220) while the fake package exhibits a different image (220').

It is noted that in the non-limiting examples, the use of InSb detector (102) allowed detection in the MWIR (at wavelengths in the range of 3-5 μm) while the use of VOx detector (202) allows detection in the LWIR (at wavelengths in the range of 8-12 μm).

Reference is now made to the following non-limiting examples, which together with the above illustrate the invention in a non-limiting fashion. It is noted that while the following non-limiting examples are based on the spatial domain in a specific time frame of 10 seconds after applying the active thermal pulse, a time domain or combination of same would result in equally valuable results.

DESCRIPTION OF NON-LIMITING EXAMPLES

General

In the following non-limiting examples FIGS. 2-17, thermography images of detected samples are shown using a detector array comprising 640×512 individual pixels in the cooled detector and 384*288 individual pixels in the uncooled detector. It should be noted that the images generated in the various experiments, as performed, include a colored display. Therefore, it is noted that the method and system of the invention allow comparison between various samples making use of differences in color, which ease the identification of any inconsistencies with the desired product, as compared to the grey scale images presented herein.

Example 1

Grain Size Monitoring (NaCl Grains of Two Different Sizes)

Figure 2B:
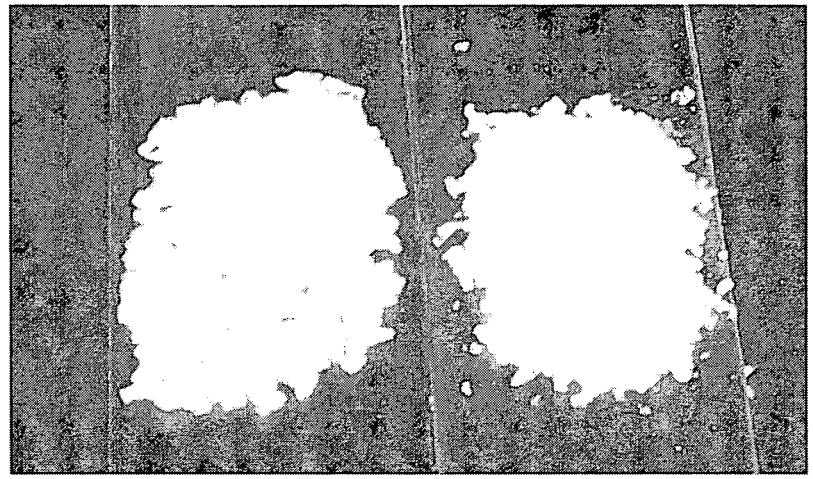
FIGS. 2A-2B show image comparison between NaCl grains of 2 mm (upper section of image) and 1 mm (lower section of image) obtained using a cooled InSb detector in the 3-5 μm wavelength range in accordance with an embodiment of the invention (FIG. 2A) or by the use of a CCD (VIS) camera (FIG. 2B).
Figure 2A:
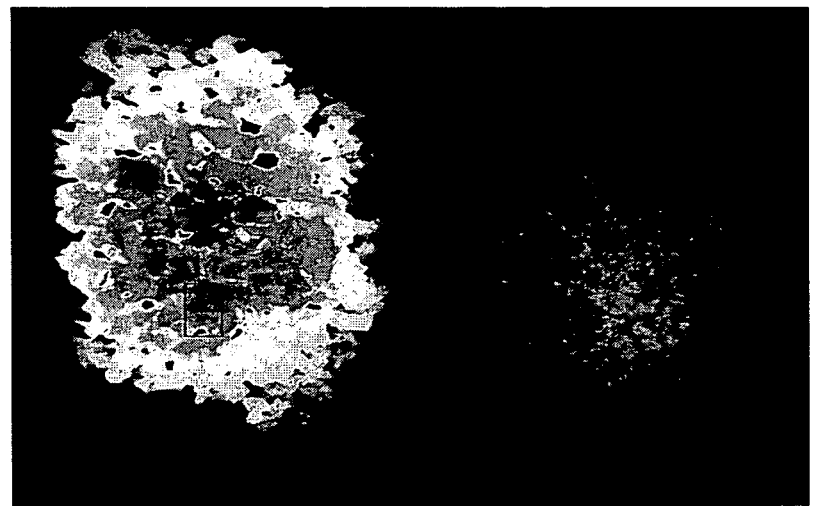

Sample Preparation:
A hand full amount of NaCl grains of a size of about 1 mm in diameter and of the size of about 2 mm in diameter were placed each on a flat glass plate on top of a Black Body radiating source.
Active Thermography:
The Black Body radiating source temperature was set to 15° C. allowing the grains temperature to reach 15° C. Subsequently the controller was set to a temperature change from 15° C. (the Black Body initial temperature) to 20° C. using a temperature step function and the image was captured 10 seconds after applying the heat target of 20° C. (the heat pulse) to the controller. A cooled InSb detector in the 3-5 μm wavelength range was used to produce an IR image of the tested samples.
Results
FIGS. 2A and 2B show a comparison between NaCl grains of different size as obtained by the method and system in accordance with one embodiment of the invention (FIG. 2A) or by a CCD (VIS) camera (FIG. 2B). Specifically, in the upper section of FIGS. 2A and 2B displayed are images of NaCl grains of a size of about 2 mm in diameter; in the lower section of FIGS. 2A and 2B displayed are images of grains of the size of about 1 mm in diameter. While difference in size of the NaCl grains can not be distinguished in the CCD images (FIG. 2B), they were clearly visualized in the thermographic images produced (FIG. 2A).

It is noted that while the resulted images were visually analyzed, without being limited thereto, the IR signal intensity of the measured powder may be analyzed by applying spatial Fourier transform on the 2D image and analyzing the dominant spatial frequencies. Subsequently, histogram and standard deviation of the 2D image may by applied. It is noted that grains of different size may be distinguished from their spatial frequencies; the larger the grains are, the lower are their dominant spatial frequency and vise versa.

Example 2

Moisture Content Monitoring (ACAMOL® Wet Vs. Dry)

Figure 3B:
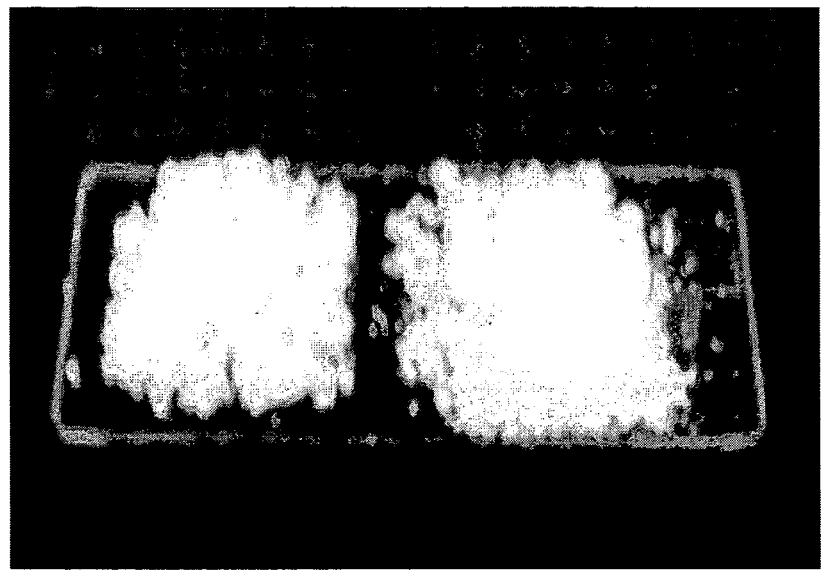
FIGS. 3A-3B show image comparison between dry (upper section of images) and wet (lower section of images) ACAMOL® powdered pills obtained using a cooled InSb detector in the 3-5 μm wavelength range in accordance with the invention (FIG. 3A) or by the use of a CCD (VIS) camera (FIG. 3B).
Figure 3A:
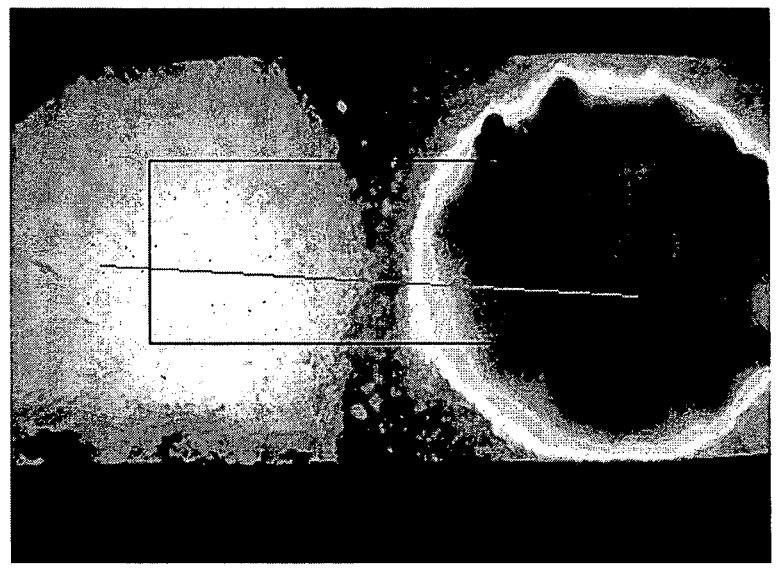

Sample Preparation:
ACAMOL® pills (Teva Pharmaceutical Industries Ltd.) were grinded and the formed powder was spread on a flat glass on top of the Black Body radiating source. Water drops of about 10 μl were splashed onto the spread material to create moisture spots.
Active Thermography:
The Black Body radiating source controller was set to a temperature change from 15° C. (the Black Body initial temperature) to 20° C. using a temperature step function and the image was captured 10 seconds after applying the heat target of 20° C. (the heat pulse) to the controller. A cooled InSb detector in the 3-5 μm wavelength range was used to produce an IR image of the detected samples.
Results
FIGS. 3A and 3B show a comparison between images of dry and moisture containing ACAMOL® powder as obtained by thermography, according to an embodiment of the invention (FIG. 3A) or by the use of a CCD (VIS) camera (FIG. 3B). Specifically, in the upper section of FIGS. 3A and 3B displayed are images taken for dry powder; in the lower section of FIGS. 3A and 3B displayed are images of moisture-containing powder. While the difference in moisture content vs. dry powder cannot be observed by the images obtained using the CCD camera (FIG. 3B), this difference is clearly evident from the thermographic images, showing in the lower section of FIG. 3A darker spots representing the wetted areas within the material which are absent from the dry ACAMOL® powder (upper section of FIG. 3A).

The resulted images were visually analyzed. However, without being limited thereto, the signal intensity of the measured ACAMOL® powder may be further analyzed by applying spatial Fourier transform on the 2D image and analyzing the dominant spatial frequencies. Subsequently band pass filters may be applied on the 2D Fourier transform to acquire the humidity spots coordinates. It is noted that wet area is characterized by a higher STD value relative to dry area. The moisture may be detected accordingly.

Example 3

Moisture Content Monitoring (ACAMOL® with Different Moisture Content)

Sample Preparation:

Two ACAMOL® pills were grinded and blended with either about 200 μl or about 50 μl of water. The two blends were spread on a flat glass on top of the Black Body radiating source.

Active Thermography:

The Black Body radiating source controller was set to a temperature change from 15° C. (the Black Body initial temperature) to 20° C. using a temperature step function and the image was captured 10 seconds after applying the heat target of 20° C. (the heat pulse) to the controller. A cooled InSb detector in the 3-5 μm wavelength range was used to produce an IR image of the detected samples. The resulted images were visually analyzed.

Results

Figure 4B:
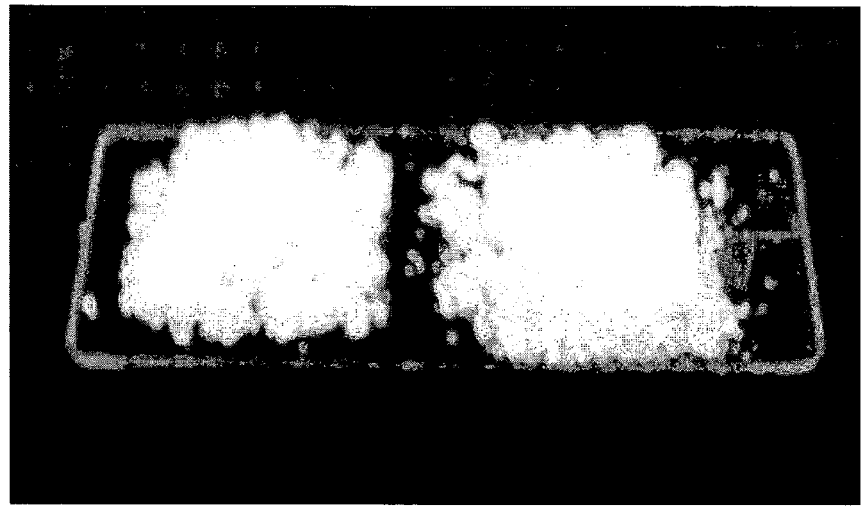
FIGS. 4A-4B show image comparison between ACAMOL® powdered pills of high (upper section of images) and low (lower section of images) moisture content obtained using a cooled InSb detector in the 3-5 μm wavelength range in accordance with an embodiment of the invention (FIG. 4A) or by the use of a CCD (VIS) camera (FIG. 4B).
Figure 4A:
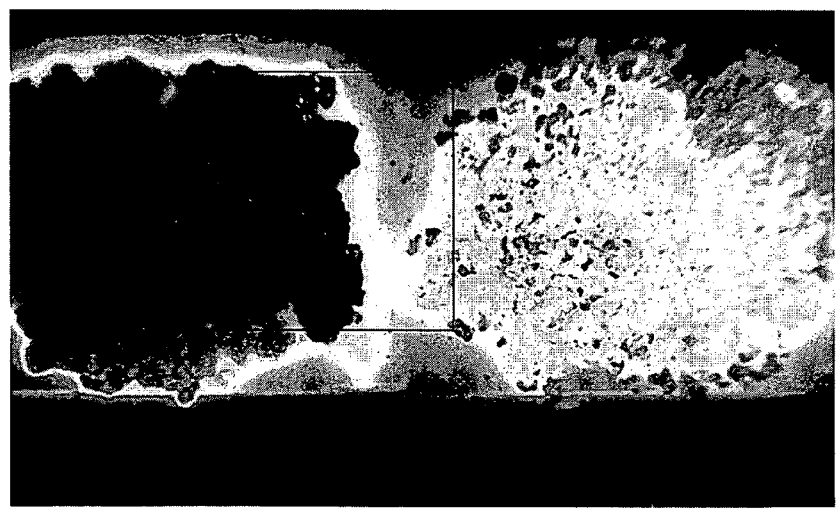

FIGS. 4A and 4B provide a comparison between images of ACAMOL® powder of high and low moisture content, where FIG. 4A display thermographic images obtained in accordance with the invention and FIG. 4B display images obtained by a CCD (VIS) camera. Specifically, in the upper section of FIGS. 4A and 4B displayed are images of ACAMOL® powder which were significantly wetted; in the lower section of FIGS. 4A and 4B displayed are images of ACAMOL® powder which, relatively to the powder in the upper section of FIGS. 4A and 4B, were only slightly wetted.

While the difference in moisture content in the powder (high vs. low moisture) cannot be observed in the CCD images (FIG. 4B), this difference is clearly evident from the thermographic images, showing in the lower section of FIG. 4A dark spots, representing the wetted powder, while the powder in the upper section of FIG. 4A is completely dark, being indicative that essentially the entire powder is wet.

The present example thus provides evidence that moisture content of a material can be detected in accordance with the invention and therefore the method of the invention may be applicable for determining quality of process where level of humidity or moisture content are crucial. The present example also provides evidence for applicability of the invention for assuring storage conditions and quality when dry conditions are required.

Example 4

Moisture Content Monitoring (Corn Flour Powder with Under Surface Moisture Spots)

Sample Preparation:

A hand full amount of corn flour was spread on a flat glass on top of the Black Body radiating source. Water drops of about 50 μl were splashed onto the material to create moisture spots. The wet spots were covered with an amount of dry corn flour powder (the amount sufficient to cover the wetted spots).

Active Thermography:

The Black Body radiating source controller was set to a temperature change from 15° C. (the Black Body initial temperature) to 20° C. using a temperature step function and the image was captured 10 seconds after applying the heat target of 20° C. (the heat pulse) to the controller. A cooled InSb detector in the 3-5 μm wavelength range was used to produce an IR image of the detected samples.

Results

Figure 5B:
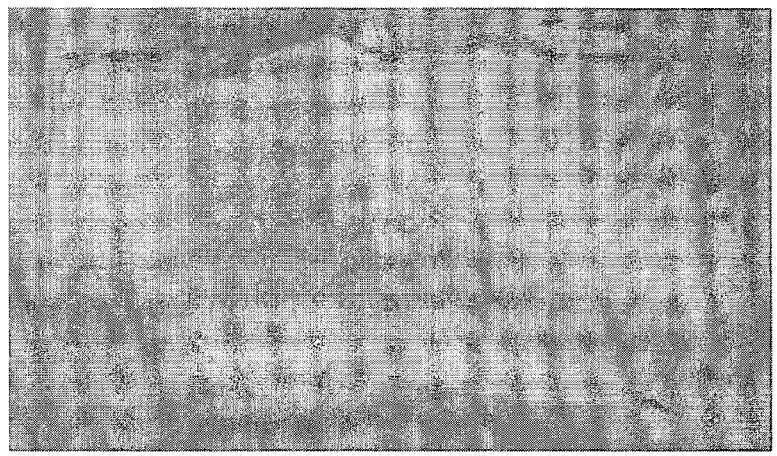
FIGS. 5A-5B show image comparison between corn flour powder of high (upper section of images, appearing as moisture spots) and low (lower section of images) moisture content obtained using a cooled InSb detector in the 3-5 μm wavelength range in accordance with an embodiment of the invention (FIG. 5A) or by the use of a CCD (VIS) camera (FIG. 5B).
Figure 5A:
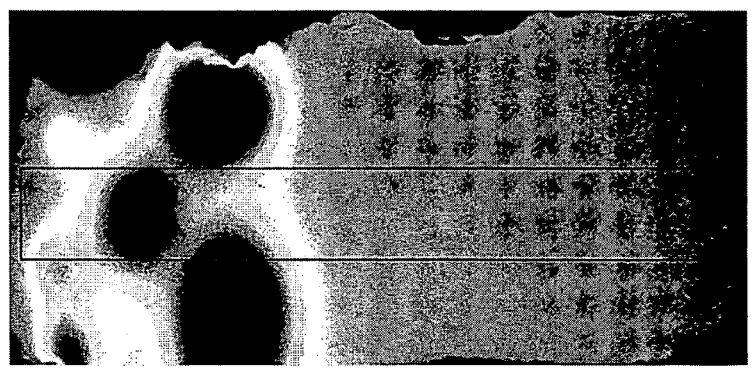

FIGS. 5A and 5B provide a comparison between images of corn flour powder of different moisture content, where FIG. 5A display thermographic images obtained in accordance with the invention and FIG. 5B display images obtained by a CCD (VIS) camera. Specifically, in the upper section of FIGS. 5A and 5B displayed are images of corn flour containing under surface moisture spots; in the lower section of FIGS. 5A and 5B displayed are images of dry corn flour powder.

While the under surface water spots cannot be observed in the CCD image (upper section of FIG. 5B), they can be clearly detected in the thermographic image showing in the upper section of FIG. 5A dark spots, representing the under surface water spots.

The resulted images were visually analyzed. Spatial Fourier transform may be applied on the 2D image and the dominant spatial frequencies may be analyzed. Additionally, band pass filters may be applied on the 2D Fourier transform to acquire the humidity spots coordinates followed by applying a 2D spatial derivation kernel in order to recognize spots boundaries (edge detection).

It is noted that the above Examples 2 to 4 provide proof of concept for the method and the system of the invention by allowing the "coloring" of different moisture containing areas in samples under examination. The "coloring" in these specific examples is related to the difference in the water content of the samples which is resulted in different IR radiation intensities. The method and system of the invention may be therefore used to monitor blending uniformity between two or more samples which are differ in their degree of humidity.

Example 5

Powder Morphology Monitoring (Corn Flour Compact/Condense Vs. Non Compact Powder Samples)

Sample Preparation:

A hand full amount of corn flour powder was manually pressed to create a smooth compact layer of material on a flat glass and placed on top of the Black Body radiating source.

Active Thermography:

The Black Body radiating source controller was set to a temperature change from 15° C. (the Black Body initial temperature) to 20° C. using a temperature step function and the image was captured 10 seconds after applying the heat target of 20° C. (the heat pulse) to the controller. A cooled InSb detector in the 3-5 μm wavelength range was used to produce an IR image of the detected samples.

Results

Figure 6B:
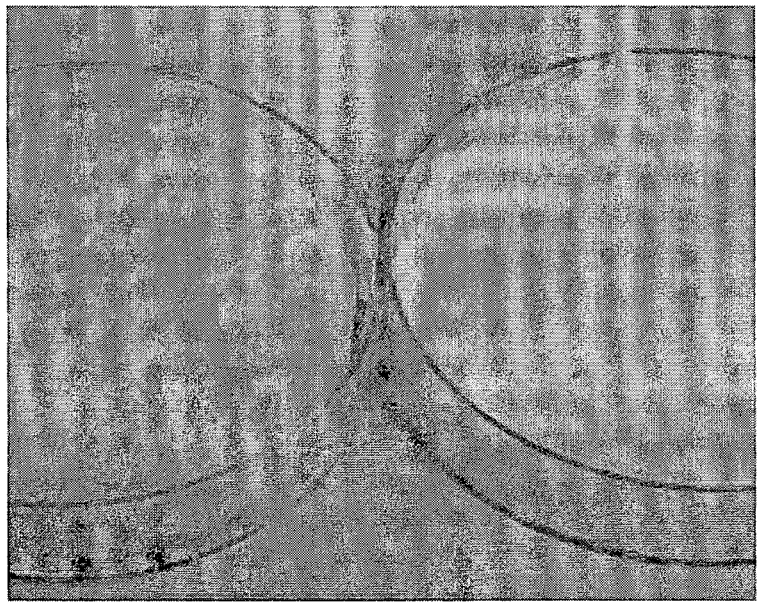
FIGS. 6A-6B show image comparison between corn flour powder of different morphology (upper sample less compact than lower sample) obtained using a cooled InSb detector in the 3-5 μm wavelength range in accordance with an embodiment of the invention (FIG. 6A) or by the use of a CCD (VIS) camera (FIG. 6B).
Figure 6A:
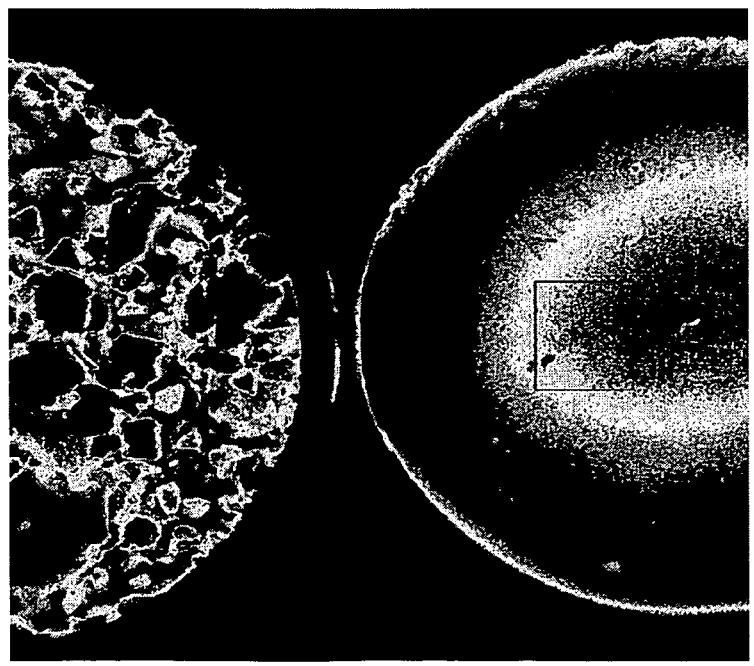

FIGS. 6A and 6B show a comparison between corn flour powder of different morphology as obtained by the method and system in accordance with one embodiment of the invention (FIG. 6A) or by a CCD (VIS) camera (FIG. 6B). Specifically, in the upper section of FIGS. 6A and 6B displayed are images of non-compacted corn flour; in the lower section of FIGS. 6A and 6B displayed are images of compacted corn flour. The compact and non-compact corn flour can be visually distinguished in the CCD images (FIG. 6B), as well as in the thermographic images (FIG. 6A).

It is noted that while the images were visually analyzed, they may also be further processed. Without being limited thereto, further processing may comprise a histogram and a standard deviation of the 2D image followed by applying spatial Fourier transform on the 2D image and analyzing the dominant spatial frequencies. A 2D spatial derivation kernel may by applied in order to recognize spots boundaries (edge detection).

Example 6

Powder Blending Monitoring (Heat "Coloring" of Corn Flour)

Sample Preparation:

Two hand full portions of corn flour, one pre-heated to 25° C. and the other pre-heated to 20° C. both on a TEC (Thermo Electric Cooler) by LAIRD Technologies, were spread on a flat glass on top of the Black Body radiating source stabled at 15° C.

Active Thermography:

The thermographic images were captured 10 sec after the samples were placed on the Black Body radiating source.

A cooled InSb detector in the 3-5 μm wavelength range was used to produce an IR image of the detected samples.

Results

Figure 7B:
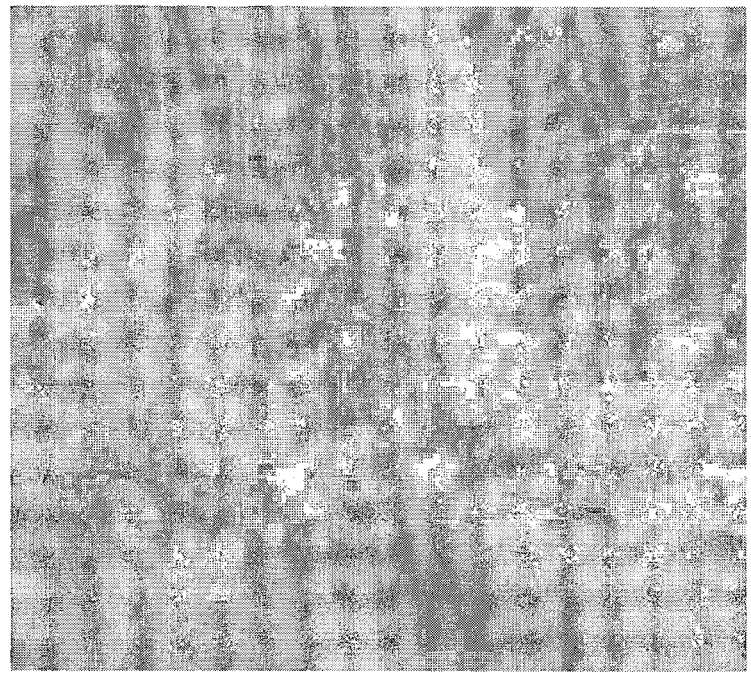
FIGS. 7A-7B show image comparison between corn flour powder at different temperatures (20° C. upper section of images, an 35° C. in lower section of images) obtained using a cooled InSb detector in the 3-5 μm wavelength range in accordance with an embodiment of the invention (FIG. 7A) or by the use of a CCD (VIS) camera (FIG. 7B).
Figure 7A:
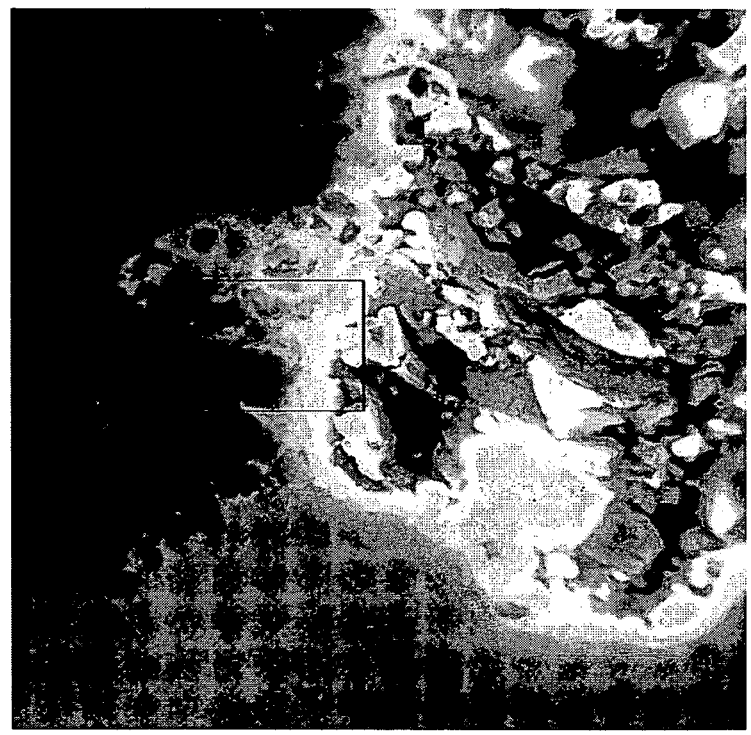

FIGS. 7A and 7B show a comparison between corn flour powder at different temperatures as obtained by the method and system in accordance with one embodiment of the invention (FIG. 7A) or by a CCD (VIS) camera (FIG. 7B). Specifically, in the upper section of FIGS. 7A and 7B displayed are images of corn flour powder at 20° C.; in the lower section of FIGS. 7A and 7B displayed are images of corn flour powder at 25° C. While no differences are observed in the CCD images of the powder at the two temperatures (FIG. 7B), the difference between the images are clearly visualized in the thermographic images produced (FIG. 7A). The specific example indicates the ability of the method and system of the invention to "color" the detected samples by means of heating or cooling. Specifically, the difference in the temperatures of the samples resulted in different intensities of the IR radiation of the detected samples. Hence, the method and system of the invention may be used to monitor the degree to which samples of various temperatures are blended.

Example 7

Monitoring of Drying Process (Temperature Distribution Characterization)

Hot air was blown on the Black Body radiating source using a fan. The hot air was monitored by the system of the invention.

Results

Figure 8B:
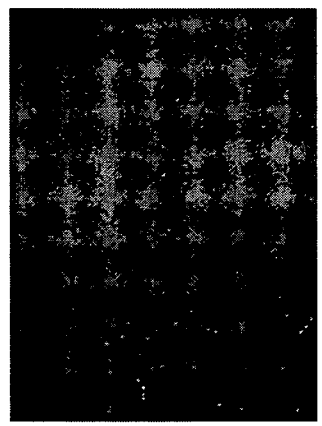
FIGS. 8A-8B show image comparison between samples subjected to hot air, where hot air distribution is observed in the image obtained in accordance with an embodiment of the invention, using a cooled InSb detector in the 3-5 μm wavelength range (FIG. 8A) and not detected when using a CCD (VIS) camera (FIG. 8B).
Figure 8A:

FIGS. 8A and 8B show a comparison between images of hot air distribution obtained in accordance with an embodiment of the invention (FIG. 8A) or by the use of a CCD (VIS) camera (FIG. 8B). It can be clearly seen that while air can not be captured by the CCD camera (FIG. 8B), hot air distribution can be visualized in the thermographic image produced (FIG. 8A). Thermography may be therefore used in real time as an indicative of the degree of homogeneity of the hot air flow for example in heating/drying/baking processes in which uniform air flow is necessary in order to achieve a uniform product. Optimization or adjustment of such processes can be thereby achieved.

Example 8

Powder Identification (CIALIS® Vs. Fake powder)

Sample Preparation:
Genuine CIALIS® drug (Eli Lilly) and a counterfeit/fake drug were grinded and spread on a flat glass on top of the Black Body radiating source.

The purpose of this example as well as the following Examples 9 and 10 is to show, inter alia, that the method and system of the invention are applicable for determining quality of an authentic product vs. a fake product.

Active Thermography:
The Black Body radiating source controller was set to a temperature change from 15° C. (the Black Body initial temperature) to 20° C. using a temperature step function and the image was captured 10 seconds after applying the heat target of 20° C. (the heat pulse) to the controller. A cooled InSb detector in the 3-5 μm wavelength range was used to produce an IR image of the detected samples.

Results

Figure 9B:
FIGS. 9A-9B show image comparison between CIALIS® genuine product (upper section of image) and a counterfeit powder (lower section of image), the image obtained using a cooled InSb detector in the 3-5 μm wavelength range in accordance with an embodiment of the invention (FIG. 9A) or by the use of a CCD (VIS) camera (FIG. 9B).
Figure 9A:
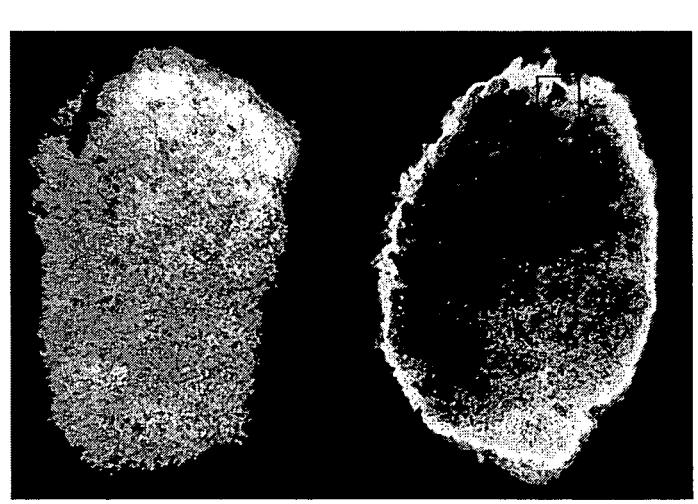

FIGS. 9A and 9B show a comparison between CIALIS® genuine powder and a counterfeit powder as obtained by the method and system in accordance with one embodiment of the invention (FIG. 9A) or by a CCD (VIS) camera (FIG. 9B). Specifically, in the upper section of FIGS. 9A and 9B displayed are images of genuine powder; in the lower section of FIGS. 9A and 9B displayed are images of counterfeit powder. While genuine and fake powder can not be distinguished in the CCD images (FIG. 9B), they are visually distinguished in the thermographic images produced (FIG. 9A).

Example 9

Drug Identification (Genuine/Authentic VIAGRA® Vs. Counterfeit Product)

Sample Preparation:
Genuine VIAGRA® (Pfizer) and counterfeit VIAGRA packages were placed on top of the Black Body radiating source.

Active Thermography:
The Black Body radiating source controller was set to a temperature change from 15° C. (the black body initial temperature) to 20° C. using a temperature step function and the image was captured 10 seconds after applying the heat target of 20° C. (the heat pulse) to the controller. An un-cooled VOx detector in the 8-12 μm wavelength range was used to produce an IR image of the detected samples.

Results

Figure 10B:
FIGS. 10A-10B show image comparison between VIAGRA® genuine package (right package in each figure) and a counterfeit package (left package in an image) obtained using an un-cooled VOx detector in the 8-12 μm wavelength range, in accordance with an embodiment of the invention (FIG. 10A) or by the use of a CCD (VIS) camera (FIG. 10B).
Figure 10A:
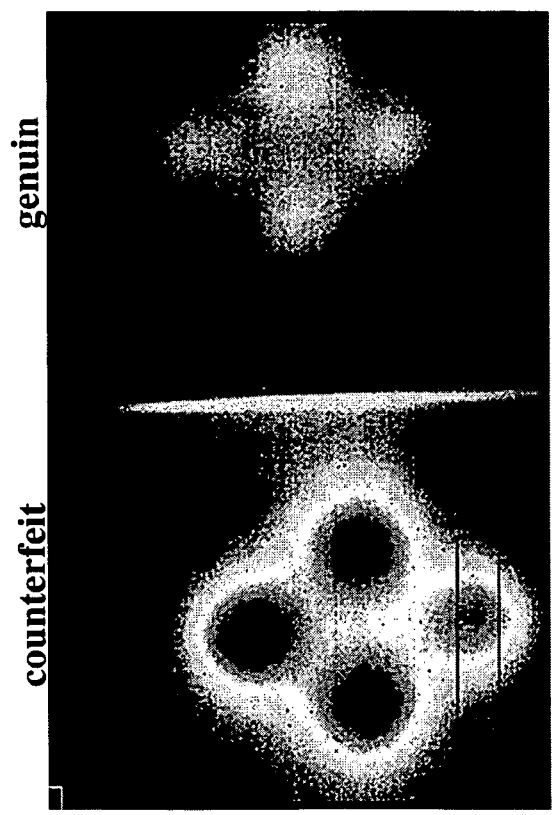

FIGS. 10A and 10B show a comparison between genuine VIAGRA® and a counterfeit VIAGRA® packages as obtained by the method and system in accordance with one embodiment of the invention (FIG. 10A) or by a CCD (VIS) camera (FIG. 10B). While genuine and fake VIAGRA® packages can not be distinguished in the CCD image (FIG. 10B), they are visually distinguished in the thermographic image produced (FIG. 10A). This example illustrates how the detection of counterfeit products, such as drugs, can be achieved. Examining a suspected counterfeit product may be by comparison to a pre-acquired IR image of the genuine product. The degree of identity may be indicative if the product is genuine or not. The pre-acquired image may be part of a database.

The above example illustrates the feasibility of the method and system of the invention to determine quality of a product within a closed package.

Example 10

Drug Identification by Fusion of Images (Genuine/Authentic VIAGRA® Vs. Counterfeit Product)

Sample Preparation:

Genuine VIAGRA® (Pfizer) and counterfeit VIAGRA packages were placed in a cooling chamber at 5° C. for two minutes. Specifically, the samples were subjected to a step heat function by cooling down in a chamber to a predefined temperature of 5° C. followed by removal of samples from the chamber and placement on a sample holder at room temperature.

Active Thermography:

The thermographic image was captured 10 seconds after the samples were taken off the chamber and placed at room temperature. A thermographic long wave bolometric VOx camera and NIR InSb camera was used to produce an IR image of the detected samples.

Results

Figure 11B:
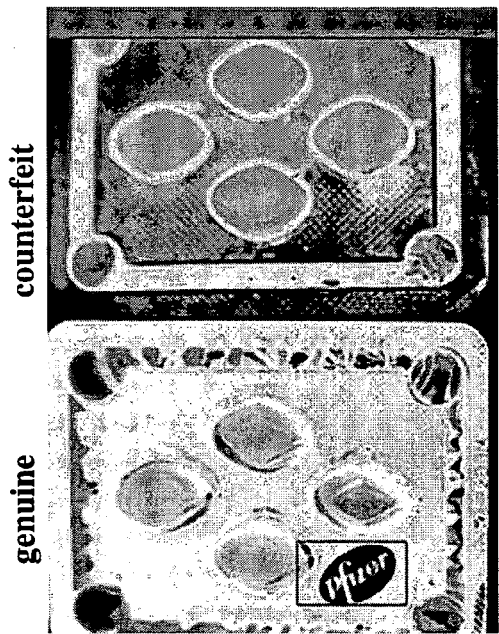
FIGS. 11A-11D show image comparison between authentic VIAGRA® and a counterfeit packages obtained with a thermographic long wave bolometric VOx camera (FIG. 11A), a NIR InSb camera (FIG. 11B) and with a CCD (VIS) camera (FIG. 11C). A fusion of the images of FIG. 11A
Figure 11D:
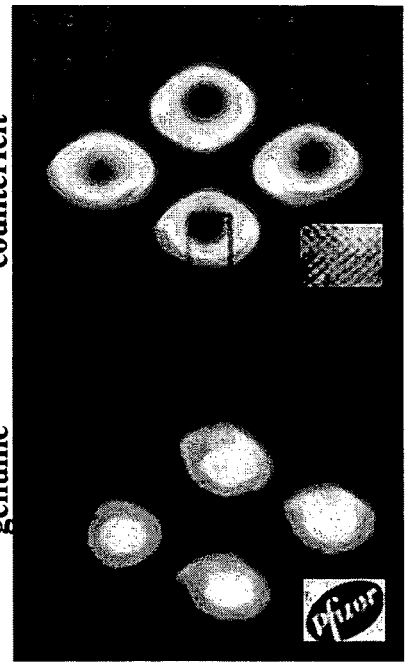
Figure 11A:
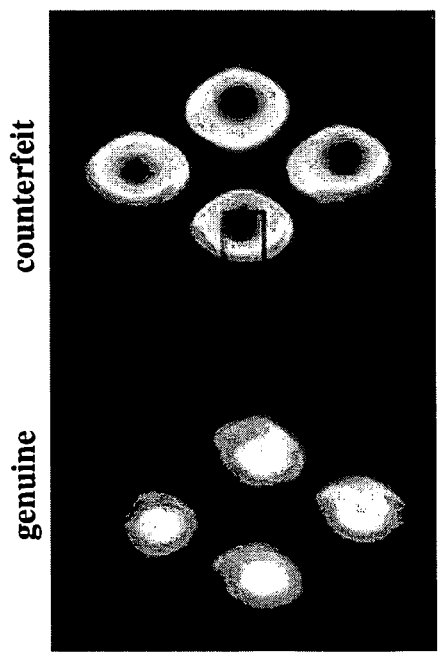
Figure 11C:
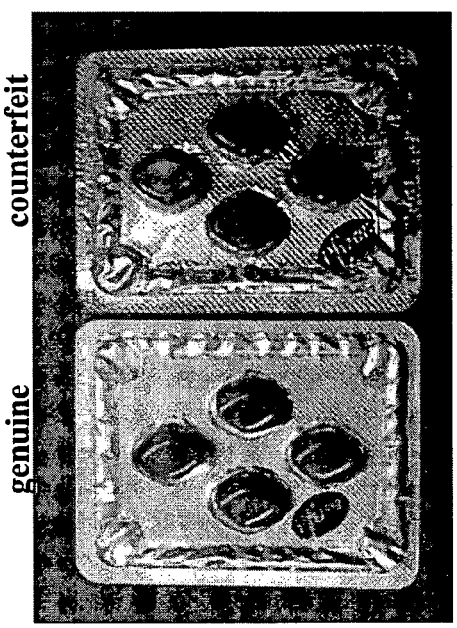

FIGS. 11A to 11D show a comparison between genuine VIAGRA® and a counterfeit VIAGRA® packages as obtained by a thermographic long wave bolometric VOx camera (FIG. 11A), by a NIR InSb camera (FIG. 11B), and by a CCD (VIS) camera (FIG. 11C). Fusion of the images obtained in FIG. 11A and FIG. 11B is shown in FIG. 11D. The difference between the authentic and the counterfeit drugs are easily detected in FIG. 11A. It is noted that the Pfizer tag of the authentic drug is observed in the NIR region while the counterfeit tag cannot be observed (FIG. 11B). It is further noted that the blue color of counterfeit drug in the VIS spectra is slightly darker then the authentic one (FIG. 11C).

The example illustrates that each spectra image of the drugs i.e., VIS, NIR, Thermal (MWIR or LWIR), contributes to some extent for counterfeit detection (or quality assurance). The example further illustrates the possibility to apply a fusion image of more than one spectrum to improve the recognition and/or detection ability.

Example 11

Dosage Inspection (ENALAPRIL® 20 mg Vs. 10 mg)

Sample Preparation:

A blister of 10 mg and a blister of 20 mg of the active component Enalapril were placed in a cooling chamber to reduce the temperature of the samples to 5° C. Specifically, the samples were subjected to a step heat function by cooling down in a chamber to a predefined temperature of 5° C. followed by removal of samples from the chamber and placement on a sample holder at room temperature.

Active Thermography:

The thermographic image was captured 10 seconds after the samples were taken off the chamber and placed in room temperature. A cooled InSb detector in the 3-5 µm wavelength range was used to produce an IR image of the detected samples.

Results

Figure 12B:
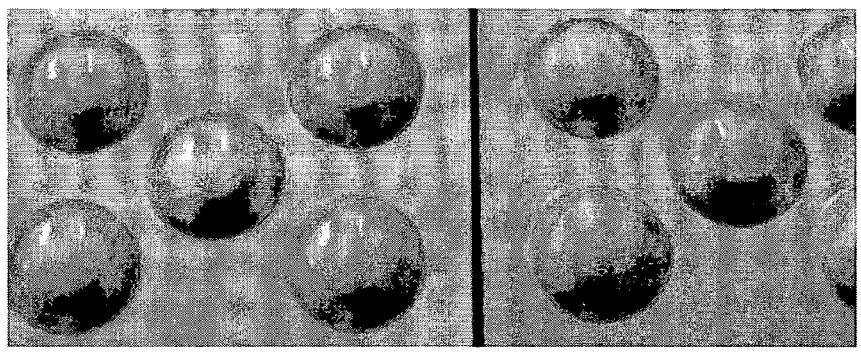
FIGS. 12A-12B show image comparison between blisters of the active compound Enalapril at different dosages obtained using a cooled InSb detector in the 3-5 μm wavelength range in accordance with an embodiment of the invention (FIG. 12A) or by the use of a CCD (VIS) camera (FIG. 12B).
Figure 12A:
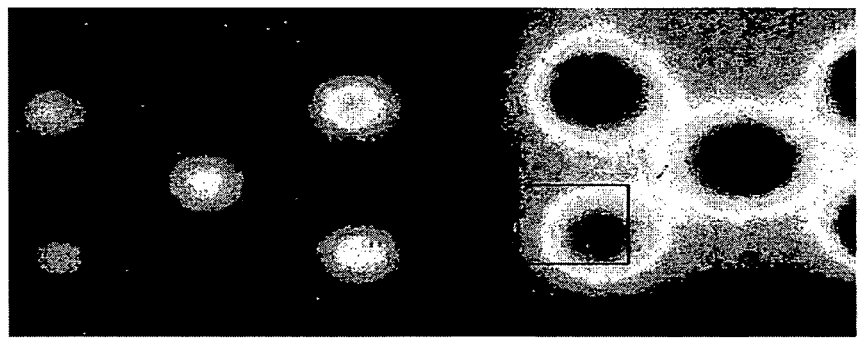

FIGS. 12A and 12B show a comparison between images of blisters of the active compound Enalapril at different dosages obtained in accordance with an embodiment of the invention (FIG. 12A) or by the use of a CCD (VIS) camera (FIG. 12B). Specifically, in the upper section of FIGS. 12A and 12B displayed are images of 10 mg dosage within the blister; in the lower section of FIGS. 12A and 12B displayed are images of 20 mg dosage. While the CCD images of the 10 mg and 20 mg dosage within the blister are identical (FIG. 12B), they are visually distinguished in the thermographic images produced (FIG. 12A) showing that the invention is applicable also for sealed materials.

This specific example shows that the method and system of the invention may be used for real time assurance that a packed product includes the product as labeled on the package. While the Example shows the difference between amounts of material (10 mg vs. 20 mg), the technology of the invention is also applicable to show the presence or absence of material, as shown further below.

Example 12

Dosage Inspection (ENALADEX® 20 mg Vs. 10 mg)

Sample Preparation:

ENALADEX® (Dexcel LTD) package containing 10 mg and a package containing 20 mg of the active component Enalapril were placed in a cooling chamber to reduce the temperature of the samples to 5° C. Specifically, the samples were subjected to a step heat function by cooling down in a chamber to a predefined temperature of 5° C. followed by removal of the samples from the chamber and placement on a sample holder at room temperature.

Active Thermography:

The thermographic image was captured 10 seconds after the samples were taken off the chamber to room temperature. A cooled InSb detector in the 3-5 µm wavelength range was used to produce an IR image of the detected samples.

Results

Figure 13A:
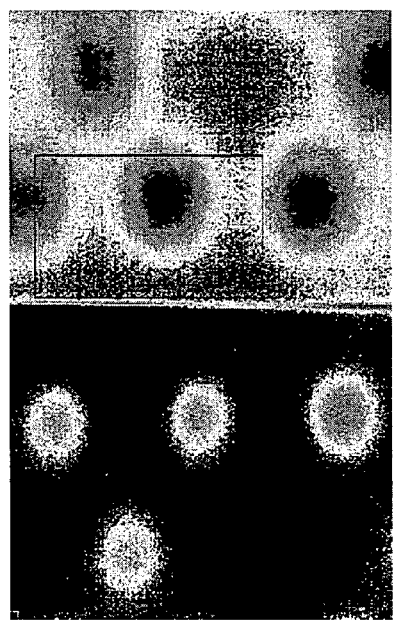
FIGS. 13A-13B show image comparison between ENALADEX® packages containing 10 mg (left side) and 20 mg (right side) of the active component Enalapril obtained using a cooled InSb detector in the 3-5 μm wavelength range, in accordance with an embodiment of the invention (FIG. 13A) or by the use of a CCD (VIS) camera (FIG. 13B).
Figure 13B:
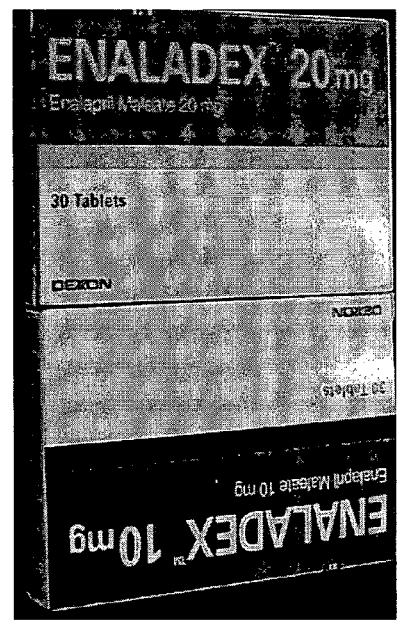

FIGS. 13A and 13B show a comparison between ENALADEX packages containing 10 mg and 20 mg of the active component Enalapril obtained in accordance with an embodiment of the invention (FIG. 13A) or by the use of a CCD (VIS) camera (FIG. 13B). Specifically, in the left section of FIGS. 13A and 13B displayed are images of a package containing 10 mg capsules; in the right section of FIGS. 13A and 13B displayed are images of a package containing 20 mg capsules. While the images of the mg and 20 mg ENALADEX packages produced by the CCD camera display the visual packages with the written information thereon (FIG. 13B), the produced thermographic images display a clear difference between the two packages indicative of the amount of the active material contained therein (FIG. 13A).

Example 13

Detection of a Broken Tablet or a Missing Tablet in a Blister

Sample Preparation:

A blister-type package containing tablets was placed in the cooling chamber at 8° C. for two minutes. Specifically, the package was subjected to a step heat function by cooling in a chamber at a predefined temperature of 8° C. followed by removal of sample from the chamber and placement on a sample holder at room temperature.

Active Thermography:

The thermographic image was captured 10 seconds after the sample was taken off the chamber to room temperature. A cooled InSb detector in the 3-5 μm wavelength range was used to produce an IR image of the detected samples.

Results

Figure 14B:
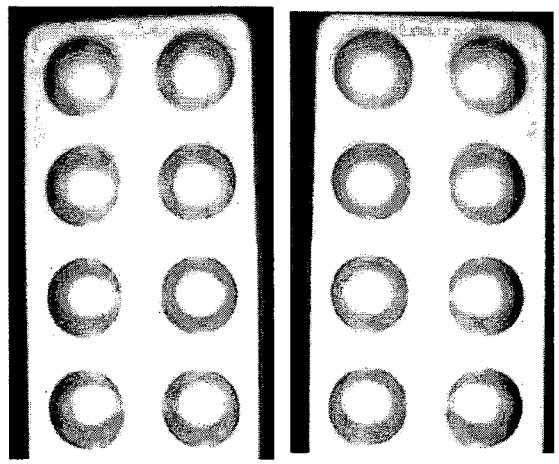
FIGS. 14A-14B show image comparison between Alu-Alu blister type packages containing tablets obtained using cooled InSb detector in the 3-5 μm wavelength range, in accordance with an embodiment of the invention (FIG. 14A) or by the use of a CCD (VIS) camera (FIG. 14B). The blisters were missing a tablet (upper pair of images) or contained a broken tablet (lower pair or images).
Figure 14A:
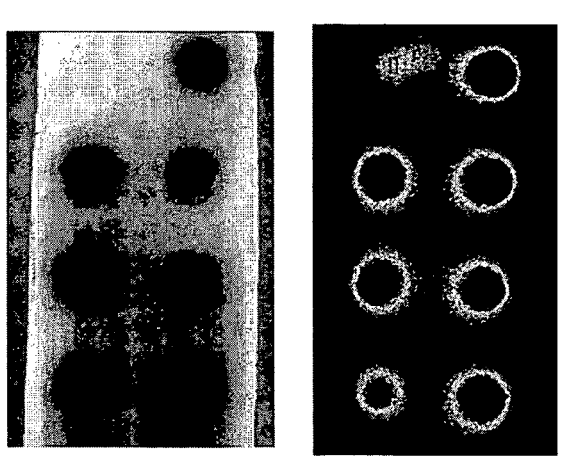

FIGS. 14A and 14B show a comparison between images of blisters obtained in accordance with an embodiment of the invention, using the cooled InSb detector (FIG. 14A) or by the use of a CCD (VIS) camera (FIG. 14B). The upper and lower sections of FIGS. 14A and 14B display images of a blister missing a tablet and the lower portions show a broken tablet. While the detection of a missing tablet or a broken tablet cannot be achieved by the CCD images (FIG. 14B), the thermographic images produced in accordance with the invention clearly indicate where there is a missing or broken tablet (FIG. 14A).

This Example illustrates that the invention may be used for quality assurance of a packed product, for example, assuring the presence of tablets in a blister, detecting defected tablets such as a broken tablet. Further, the example shows that the invention may be used to identify defects in coating of a tablet or a defected capsule while being contained in a blister.

Example 14

Monitoring Liquid Level in Sealed Bottles

Sample Preparation:

Two Opaque bottles containing different amount of water were placed in a cooling chamber at 8° C. for two minutes. Specifically, the bottles were subjected to a step heat function by cooling down in a chamber to a predefined temperature of 8° C. followed by removal of sample from the chamber and placement on a sample holder at room temperature.

Active Thermography:

The thermographic image was captured 10 seconds after the bottles were taken off the chamber and placed at room temperature. A cooled InSb detector in the 3-5 μm wavelength range was used to produce an IR image of the detected bottles.

Results

Figure 15A:
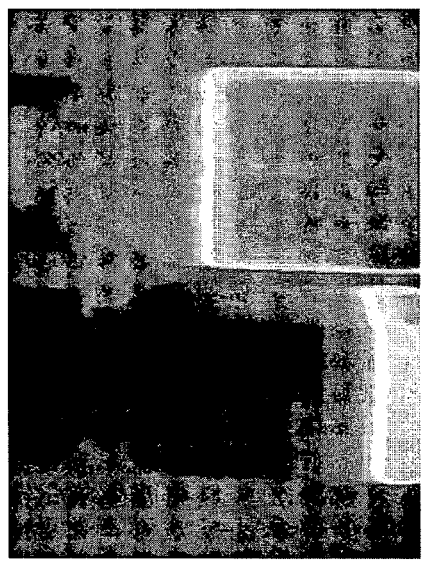
FIGS. 15A-15B show image comparison between two opaque bottles containing different amounts of water, the images obtained using either cooled InSb detector in the 3-5 μm wavelength range, in accordance with the invention (FIG. 15A) or by the use of a CCD (VIS) camera (FIG. 15B).
Figure 15B:
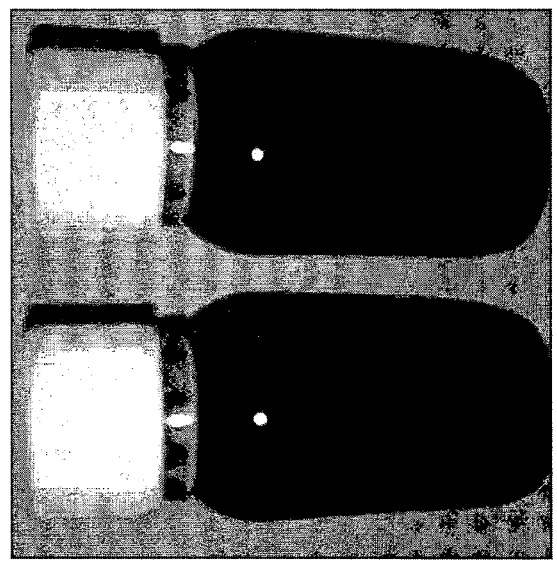

FIGS. 15A and 15B show a comparison between images of bottles containing different amount of water as obtained in accordance with an embodiment of the invention (FIG. 15A) or by the use of a CCD (VIS) camera (FIG. 15B). While the content of the two bottles can not be distinguished using a CCD image (FIG. 15B), they are visually distinguished in the thermographic image produced, i.e. the different level of water contained in the bottles is clearly detected although the bottles per se are opaque and sealed and their content is invisible to the eye (FIG. 15A).

This example illustrates that the invention is also applicable for detecting content of material within sealed containers. The type of the container and the material it is made of irrelevant for performing the invention. The invention is applicable for any type of container, e.g. plastic bottle, dark glass bottle, tape covered bottle etc.

At times, the detection of liquid level in a container may be improved if the liquid is cooler than the bottle, e.g. detection immediately after introduction of the liquid to the bottle. When the cooled liquid is introduced into the bottle it cools the bottles inner wall only, and only to a temperature of the liquid, while the rest of the bottle stays at its original temperature. This may allow real time assurance that the accurate amount of liquid was introduced into the bottle during the packing in a manufacturing process.

Example 15

Beverages Distinguishing (BARKAN Vs. SEGAL Cabernet Sauvignon)

Sample Preparation:

A bottle of BARKAN® dry red wine and two bottles of SEGAL® Cabernet Sauvignon dry red wine were placed on a Black Body radiation source and heated to 30° C. Specifically, the wine bottles were subjected to a step heat function as they were taken off the Black Body radiation source and placed at ambient room temperature (23° C.).

Active Thermography:

The thermographic image was captured 10 seconds after the bottles were taken off the Black Body radiation source and placed at ambient room temperature (23° C.). A cooled InSb detector in the 3-5 μm wavelength range was used to produce an IR image of the detected bottles.

Results

Figure 16A:
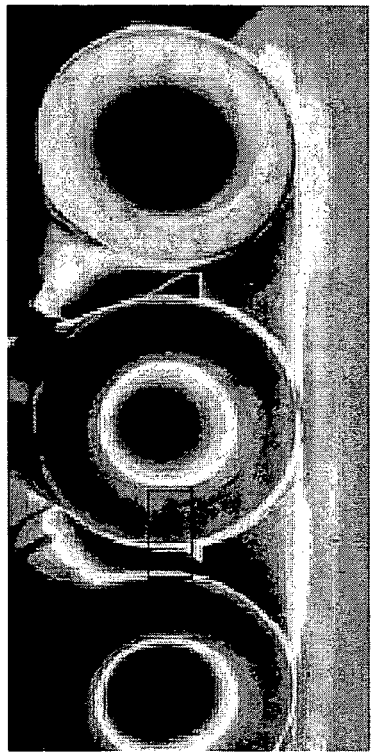
FIGS. 16A-16B show image comparison between two types of dry red wine bottles, a first produced by BARKAN® winery and the second by SEGAL® winery, the images obtained using a cooled InSb detector in the 3-5 μm wavelength range, in accordance with the invention (FIG. 16A) or by the use of a CCD (VIS) camera (FIG. 16B).
Figure 16B:
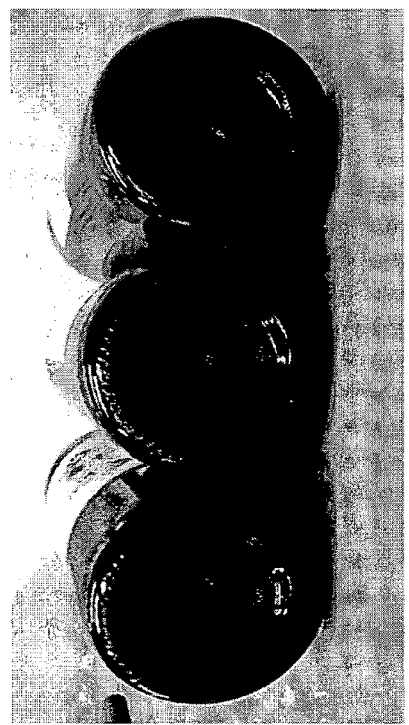

FIGS. 16A and 16B show a comparison between images of one bottle of BARKAN® (right bottle) and two bottles of SEGAL® (mid and left bottles) Cabernet Sauvignon dry red wine obtained in accordance with an embodiment of the invention (FIG. 16A) or by the use of a CCD (VIS) camera (FIG. 16B). While the BARKAN® and SEGAL® bottles of wine can not be distinguished when using a CCD device (FIG. 16B), the difference in the bottles can be easily visualized using the thermographic image (FIG. 16A). Thus, this example illustrates how the recognition of various brands of beverages, such as wine bottles, can be achieved by the invention. In other words, the invention should not be limited to pharma industry but also to any product manufacturing process, such as winery.

Example 16

Detection of Foreign Objects

Sample Preparation:

Plastic particles were spread on a plate containing white sugar grains. The plate was placed on a Black Body radiation source at a temperature of 25° C. The mixture of sugar and plastic particles was subjected to a step cooling function by reducing the temperature of the Black Body radiation source to 15°.

Active Thermography:

The thermographic image was captured 10 seconds after applying the step function. A cooled InSb detector in the 3-5 μm wavelength range was used to produce an IR image of the detected sample.

Results

Figure 17B:
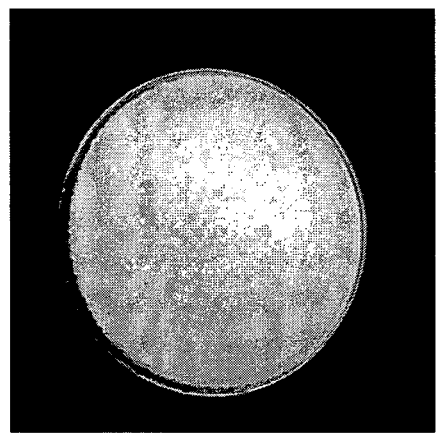
FIGS. 17A-17B show image comparison between white sugar grains containing plastic particles, the images using a cooled InSb detector in the 3-5 μm wavelength range in accordance with the invention (FIG. 17A) or by the use of a CCD (VIS) camera (FIG. 17B).
Figure 17A:
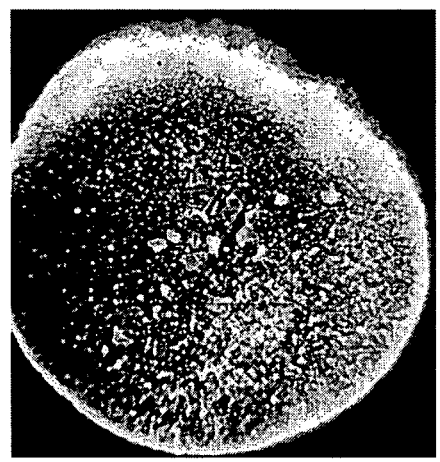

FIGS. 17A and 17B show a comparison between images of white sugar grains containing plastic particles according to an embodiment of the invention (FIG. 17A) or by the use of a CCD (VIS) camera (FIG. 17B). While the presence of the plastic particles can not be detected using a CCD camera they can be clearly observed in the thermographic image.

This example illustrates how the invention may be used for detection of foreign objects in food products.

Example 17

Detection of Authenticity of a Package or Defects in a Package (1) Packages of an authentic drug and of a fake drug were placed side by side on a sample holder and illuminated with a Halogen lamp (35 Watt). A near IR snapshot image was acquired using InSb cooled detector (SCD manufactured) and 20 mm focal lenses. A difference was exhibited between the image of the authentic package and that of the fake package (not shown). Thus, NIR images of samples under illumination can be used to determine authenticity of a package, e.g. of a drug.

(2) Packages of an authentic drug and of a fake drug were placed side by side on a sample holder and illuminated. A snapshot image was captured in the visible wavelength using CMOS detector with 1.4 mega pixel and 20 mm focal length lenses and a standard electric bulb lamp light illuminating the packages. A difference between the packages was detected, ensuring identification of authentic vs. fake packages.

The invention claimed is:

1. A method for determining quality of material obtained in a manufacturing process comprising:
   (a) generating an infrared (IR) thermographic image of said material by an IR detector operable to sense, in its field of view, radiation of said material in a mid to very long IR wavelength;
   (b) in a spatial domain, processing the IR thermographic image to generate an output indicative of the quality of said material and which comprises at least one material parameter selected from the group consisting of moisture content, moisture dispersion, density, particle size, polymorphic structures, crystal structure, temperature, temperature distribution, material homogeneity, morphology, texture, coating quality, porosity, material integrity, missing material and authenticity of the material; and
   (c) correlating said material parameter with a predetermined threshold parameter for said manufacturing process, said threshold parameter comprises an essentially distinct value or a range of values representing a desired quality of the material prepared in said manufacturing process; and
   (d) utilizing said output to alter the manufacturing process when said material parameter is different from said threshold parameter or is outside the range of values of said threshold parameter,
   wherein said manufacturing process provides a product selected from a therapeutic product, a beverage, a cosmetic product, a food product or a food supplemental.

2. The method of claim 1, wherein said thermographic image is generated by active thermography and said active thermography comprises applying onto said material a single thermal pulse or a sequence of two or more thermal pulses.

3. The method of claim 2, wherein said thermal pulse is selected from heating said material, cooling said material, cooling followed by heating of said material and heating followed by cooling said material.

4. The method of claim 1, wherein said mid to very long IR wavelength comprises any wavelength in the range selected from the group consisting of from 3 μm to 20 μm, from 8 μm to 12 μm, from 7 μm to 14 μm, from 5 μm to 8 μm, and from 3 μm to about 5 μm.

5. The method of claim 1, wherein said IR image is generated by said IR detector in combination with an optical arrangement for focusing said radiation of said material on the IR detector.

6. The method of claim 1, where said IR image is combined with one or more images of said material obtained in the NIR, VIS, UV.

7. A system for determining quality of material obtained in a manufacturing process comprising:
   (a) an IR image generating device comprising an IR detector operable to sense, in its field of view, radiation of said material in a mid to very long IR wavelength and to generate therefrom a respective IR thermographic image of said material;
   (b) a processing utility for processing in a spatial domain said IR image to generate an output indicative of the quality of said material and which comprises at least one material parameter selected from the group consisting of moisture content, moisture dispersion, density, particle size, polymorphic structures, crystal structure, temperature, temperature distribution, material homogeneity, morphology, texture, coating quality, porosity, material integrity, missing material and authenticity of the material, wherein said processing utility is operable to correlate said material parameter with a predetermined threshold parameter for said manufacturing process, said threshold parameter comprises an essentially distinct value or a range of values representing a desired quality of the material prepared in said manufacturing process;
   (c) a control unit configured to utilize said output to alter the manufacturing process when said material parameter is different from said threshold parameter or is outside the range of values of said threshold parameter;
   wherein said manufacturing process provides a product selected from a therapeutic product, a beverage, a cosmetic product, a food product or a food supplemental.

8. The system of claim 7, wherein said thermographic image is generated by an active thermography and said system comprises a thermal pulse generator operable to apply at least one thermal pulse onto said material, the thermal pulse source is configured to apply onto said material a single thermal pulse or a sequence of two or more thermal pulses.

9. The system of claim 7, wherein said mid to very long IR wavelength comprise any wavelength in the range selected from the group consisting of from 3 μm to 20 μm, from 8 μm to 12 μm, from 7 μm to 14 μm, from 5 μm to 8 μm, and from 3 μm to about 5 μm.

10. The system of claim 7, comprising a memory comprising a database of predetermined threshold parameters of manufacturing processes, each threshold parameter is an essentially distinct value or a range of values representing a desired quality of a material to be obtained in a manufacturing process associated with said predetermined threshold, and said material parameter is correlatable with a threshold parameter from said database.

11. The system of claim 10, wherein said database of predetermined threshold parameters comprises for each threshold parameter an essentially distinct value or a range of values representing a desired quality of a material to be obtained in a manufacturing process associated with said predetermined threshold.

12. The system of claim 7, wherein when said output is indicative of a defect in said material, said control unit is operable to alter said manufacturing process by one or more of ceasing the process, repeating the process, directing the material to a different manufacturing process, altering process conditions.

* * * * *

UNITED STATES PATENT AND TRADEMARK OFFICE
CERTIFICATE OF CORRECTION

PATENT NO. : 9,008,408 B2  
APPLICATION NO. : 13/147867  
DATED : April 14, 2015  
INVENTOR(S) : Sinbar et al.

Page 1 of 1

It is certified that error appears in the above-identified patent and that said Letters Patent is hereby corrected as shown below:

IN THE CLAIMS

In claim 2, under column 21, line 45, please change "wherein said thermographic" to --wherein said IR thermographic--.

In claim 5, under column 21, line 58, please change "said IR image is" to --said IR thermographic image is--.

In claim 7, under column 22, line 9, please change "said IR image to generate" to --said IR thermographic image to generate--.

In claim 8, under column 22, line 33, please change "wherein said thermographic" to --wherein said IR thermographic--.

Signed and Sealed this  
Ninth Day of February, 2016

Michelle K. Lee  
*Director of the United States Patent and Trademark Office*